US010022338B2

(12) United States Patent
Plettner et al.

(10) Patent No.: US 10,022,338 B2
(45) Date of Patent: Jul. 17, 2018

(54) HONEY BEE MITE DISRUPTIVE COMPOUNDS AND METHODS OF APPLICATION

(71) Applicants: SIMON FRASER UNIVERSITY, Burnaby (CA); THE STATE OF ISRAEL, MINISTRY OF AGRICULTURAL & RURAL DEVELOPMENT, AGRICULTURAL RESEARCH ORGANIZATION (ARO), Bet-Dagan (IL)

(72) Inventors: Erika Plettner, Burnaby (CA); Victoria Soroker, Misgav Dov (IL)

(73) Assignees: Simon Fraser University, Burnaby, British Columbia (CA); The State of Israel, Ministry Of Agriculture & Rural Development, Agricultural Research Organization (ARO) (Volcani Center), Bet-Dagan (IL)

( * ) Notice: Subject to any disclaimer, the term of this patent is extended or adjusted under 35 U.S.C. 154(b) by 4 days.

(21) Appl. No.: 15/128,870

(22) PCT Filed: Mar. 24, 2015

(86) PCT No.: PCT/CA2015/000174
§ 371 (c)(1),
(2) Date: Sep. 23, 2016

(87) PCT Pub. No.: WO2015/143536
PCT Pub. Date: Oct. 1, 2015

(65) Prior Publication Data

US 2017/0209392 A1 Jul. 27, 2017

Related U.S. Application Data

(60) Provisional application No. 61/969,742, filed on Mar. 24, 2014.

(51) Int. Cl.
*A61K 31/09* (2006.01)
*A61K 31/075* (2006.01)
(Continued)

(52) U.S. Cl.
CPC ............ *A61K 31/09* (2013.01); *A61K 31/075* (2013.01); *A61K 36/00* (2013.01); *A61K 45/06* (2013.01);
(Continued)

(58) Field of Classification Search
CPC ...................................................... A61K 31/09
See application file for complete search history.

(56) References Cited

U.S. PATENT DOCUMENTS 5,135,758 A 8/1992 Arnold et al.
2010/0160451 A1 6/2010 Plettner et al.

FOREIGN PATENT DOCUMENTS

EP 2 301 357 A2 3/2011

OTHER PUBLICATIONS

Bioorganic & Medicinal Chemistry (2010), 18(8), 2920-2929.*
(Continued)

*Primary Examiner* — Benjamin Packard
(74) *Attorney, Agent, or Firm* — Christensen O'Connor Johnson Kindness PLLC

(57) ABSTRACT

This disclosure describes compounds that affect the olfactory responses of the honey bee mite (*Varroa destructor*) and methods of use thereof. The compounds do not kill *Varroa destructor*, and are therefore unlikely to generate *Varroa destructor* resistance, compared to an acaricide. The compounds can work in conjunction with other mite control approaches, such as a bottom board excluder and sticky board control devices, and can enhance the performance of other forms of mite control while decreasing disadvantages associated therewith.

6 Claims, 10 Drawing Sheets

3a{*2,2*}: ortho $R_1 = C_2H_5$, $R_2 = C_2H_5$
3b{*2,2*}: meta $R_1 = C_2H_5$, $R_2 = C_2H_5$
3c{*1,1*}: para $R_1 = CH_3$, $R_2 = CH_3$
3c{*1,3*}: para $R_1 = CH_3$, $R_2 = C_3H_7$
3c{*2,2*}: para $R_1 = C_2H_5$, $R_2 = C_2H_5$
3c{*2,3*}: para $R_1 = C_2H_5$, $R_2 = C_3H_7$

3a-c{$R_1$,$R_2$} cy {*1,1*}: $R_3 = CH_3$
cy {*2,1*}: $R_3 = C_2H_5$
cy {*3,1*}: $R_3 = C_3H_7$
cy {*4,1*}: $R_3$ = n-butyl
cy {*5,1*}: $R_3$ = n-pentyl cy{$R_3$,*1*}

(51) Int. Cl.
*A61K 45/06* (2006.01)
*A61K 36/00* (2006.01)
*C12N 15/113* (2010.01)

(52) U.S. Cl.
CPC ........ *C12N 15/113* (2013.01); *C12N 2310/14* (2013.01)

(56) References Cited

OTHER PUBLICATIONS

Hao Chen et al., "Synthesis and biological activity of conformationally restricted gypsy moth pheromone mimics," Bioorganic & Medicinal Chemistry, vol. 18, No. 8, Apr. 1, 2010, pp. 2920-2929, XP055391150, GB, ISSN: 0968-0896, DOI: 10.1016/j.bmc2010.02.061.
Erika Plettner et al., "Discovery of varroa mite deterrents," Abstracts of Papers, 248th ACS National Meeting & Exposition, San Francisco, CA, United States, Aug. 10-14, 2014, AGRO-712 Publisher American Chemical Society, Washington, D.C., CODEN: 69SZG4, 2014, XP009194928.
Extended European Search Report dated Aug. 4, 2017, for European Application No. 15769542.0, filed Mar. 24, 2015, 10 pages.
Eliash, N., et al., "Can We Disrupt the Sensing of Honey Bees by the Bee Parasite *Varroa destructor*?" PLOS One 9(9):e106889, Sep. 2014, 13 pages.
Akhtar, Y., et al., "Screening of Dialkoxybenzenes and Disubstituted Cyclopentene Derivatives Against the Cabbage Looper, *Trichoplusia ni*, for the Discovery of New Feeding and Oviposition Deterrents," Journal of Agricultural and Food Chemistry 55(25):10323-10330, 2007.
Corrected Version of the International Search Report and Written Opinion dated Jun. 30, 2015, issued in corresponding International Application No. PCT/CA2015/000174, filed Mar. 24, 2015, 12 pages.
Ebrahimi, Insect P., et al., "Partition, Sorption and Structure Activity Relation Study of Dialkoxybenzenes that Modulate Insect Behavior," Chemosphere 93:54-60, 2013.
Eliash, N., et al., "Can We Disrupt the Sensing of Honey Bees by the Bee Parasite *Varroa destructor*?" PLOS One 9(9):1-13, Sep. 2014.
International Search Report and Written Opinion dated Jun. 10, 2015, issued in corresponding International Application No. PCT/CA2015/000174, filed Mar. 24, 2015, 10 pages.
Paduraru, P.M., et al., "Synthesis of Substituted Alkoxy Benzene Minilibraries, for the Discovery of New Insect Olfaction or Gustation Inhibitors," Journal of Combinatorial Chemistry 10(1):123-134, 2008.

* cited by examiner

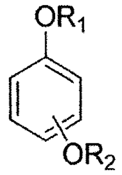

3a-c{$R_1$,$R_2$}

3a{2,2}: ortho $R_1$ = $C_2H_5$ , $R_2$ = $C_2H_5$
3b{2,2}: meta $R_1$ = $C_2H_5$ , $R_2$ = $C_2H_5$
3c{1,1}: para $R_1$ = $CH_3$ , $R_2$ = $CH_3$
3c{1,3}: para $R_1$ = $CH_3$ , $R_2$ = $C_3H_7$
3c{2,2}: para $R_1$ = $C_2H_5$ , $R_2$ = $C_2H_5$
3c{2,3}: para $R_1$ = $C_2H_5$ , $R_2$ = $C_3H_7$

FIG. 1A

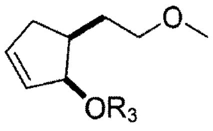

cy{$R_3$,1} cy {1,1}: $R_3$ = $CH_3$
cy {2,1}: $R_3$ = $C_2H_5$
cy {3,1}: $R_3$ = $C_3H_7$
cy {4,1}: $R_3$ = n-butyl
cy {5,1}: $R_3$ = n-pentyl

FIG. 1B

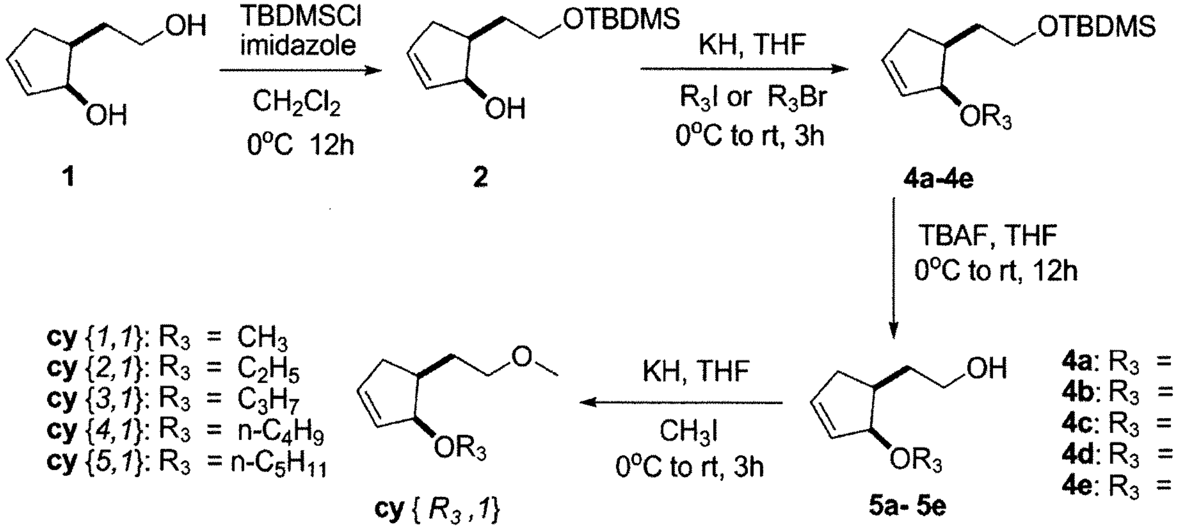

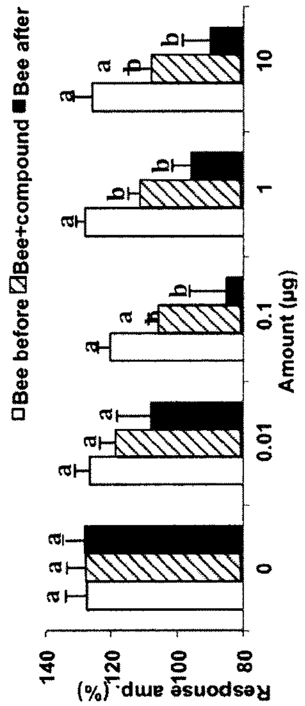
FIG. 4A
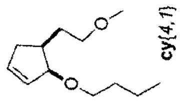
cy{4,1}
FIG. 4B
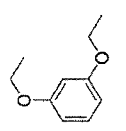
3b{2,2}
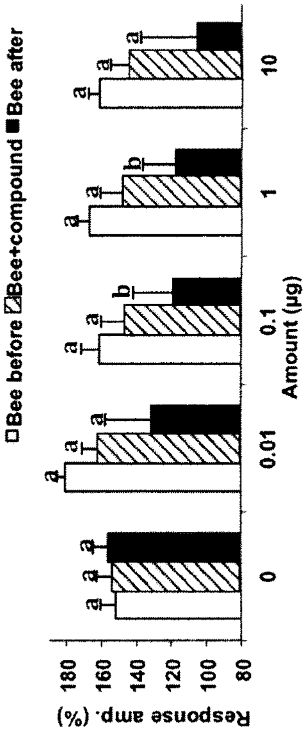
FIG. 4C
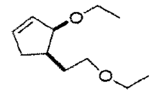
cy{2,2} cy{4,1}

3b{2,2}

3c{2,2}

HONEY BEE MITE DISRUPTIVE COMPOUNDS AND METHODS OF APPLICATION

CROSS-REFERENCE TO RELATED APPLICATION

This application claims the benefit of U.S. Patent Application No. 61/969,742, filed Mar. 24, 2014, the disclosure of which is incorporated by reference herein in its entirety.

BACKGROUND

The mite *Varroa destructor* ("*Varroa*") is a honey bee (*Apis mellifera*) ectoparasite that causes extensive colony losses. *Varroa* destroys bee colonies for two main reasons: the mites feed on the bee's hemolymph, thereby weakening them; and they transmit pathogens, such as the Israel acute paralysis virus (IAPV) and the deformed wing virus, that can cause crippling bee diseases. The mites are not easy to detect, and they can cause a seemingly healthy and productive honey bee colony to collapse within a few weeks.

*Varroa* is now considered to be one of the most significant threats to apiculture around the world. For example, in Canada, *Varroa* was first detected in New Brunswick in 1989. In 2013, all provinces in Canada had the mite, and reported mites that were resistant to the treatments used to combat them. In Israel, *Varroa* was first detected in 1984. Indeed, since *Varroa* jumped hosts from the Asian honey bee (*Apis cerana*) to the European honey bee (*Apis mellifera*), the mites have spread nearly worldwide. As of 2010, only a few islands or isolated regions, such as Australia, the Southern part of New Zealand, Newfoundland and Madagascar do not have the mite. Furthermore, due to local warm climatic conditions, *Varroa* reproduction continues year round, making it impossible to grow bees without efficient *Varroa* control.

Several different synthetic acaricides have been implemented against the *Varroa* mite. However, over the years, *Varroa* developed resistance to pyrethroids and recently to Coumaphos (CheckMite+), rendering these acaricides ineffective and thus leaving local apiculture in a very problematic condition.

Currently available chemical control methods have certain disadvantages. For example, amitraz (an acaricide), causes problems of resistant *Varroa* and honey contamination; fluvalinate (e.g., Apistan® strips), a pyrethroid, causes problems of resistant *Varroa*; coumaphos (e.g., CheckMite+™ strips, an organophosphate) causes problems of resistant *Varroa*, and its interaction with fluvalinate causes bee mortality; natural hops extract (e.g., Hopguard®) causes potential *Varroa* resistance; thyme essential oil also causes potential *Varroa* resistance; and formic acid and oxalic acid can cause bee mortality and have variable success in control of low infestation levels, but are not effective in severe infestations and are problematic for implementation in areas with hot climate.

Current available physical control methods also have drawbacks. For example, fine sugar powder can be used to abrade *Varroa* cuticles, however, it has highly variable effectiveness in controlling *Varroa*, ranging from no control to moderate *Varroa* reductions. As another example, a frame heater can be used to exploit the differential heat sensitivity of *Varroa* and brood (*Varroa* is more susceptible to heat than the bee brood), however, its use is very labor intensive and disruptive to the colony. Drone brood frames can be actively removed and destroyed, particularly because *Varroa* is more prevalent on drone brood. However, drone brood frame removal and destruction are only effective for minor mite control, are very labor intensive and do not completely remove the mites. As yet another example, bottom board excluders and sticky boards reduce the likelihood that *Varroa* that have fallen off bees can re-enter the hive. However, bottom board excluders and sticky boards only remove some of the mites.

As discussed above, available disruptive compounds and methods generally do not provide high efficiency protection against *Varroa*. However, it is believed that chemical cues can play an important role in modulating host-parasite interactions. For example, parasites often eavesdrop on their host's chemical signals, and rely on these signals for host detection and choice. Parasitism of social insects is an especially complex case, as numerous chemical signals, known as semiochemicals, are important for the function of the society, including its protection from inquilines. Although semiochemicals are well-known tools in pest management, in the enclosed and crowded environment of the colony, the proximity between the host and parasites presents an obstacle for parasite (e.g., *Varroa*) control without damaging the host (e.g., *Apis mellifera*).

*Varroa* life cycle can be generally divided into two main phases: a phoretic phase, in which the *Varroa* is parasitizing an adult bee, and a reproductive phase, in which the *Varroa* is reproducing within a sealed brood cell. Between these phases *Varroa* move freely on the surface of the comb. The entrance of the fertilized *Varroa* female into a brood cell is synchronized with the developmental stage of the honey bee larvae, and occurs just before the cell is capped. It is believed that semiochemicals play a major role in the host-finding and preference of *Varroa*. For example, in laboratory bioassays, *Varroa* has been shown to discriminate between bees from different task groups, and to prefer a nurse over a forager. The host preference is apparently based on compounds with low volatility, such as cuticular hydrocarbons, and on volatile compounds emitted by the honey bees and their environment (such as larval food and brood pheromone). Despite much progress in the identification of host olfactory cues guiding *Varroa*, neither effective attractants nor repellents have been found so far. In view of limited success in exploiting hive semiochemicals in *Varroa* control, the use of synthetic disruptive compounds can be another approach for confronting the mite.

Furthermore, the olfactory organ of the *Varroa* is located on the distal part of its forelegs, analogous to the sensory pit (Haller's organ) found in ticks. Although chemosensory sensilla in a mite's sensory pit appear similar to those described in insects, not much is known about the mechanism behind odorant detection in mites in general and *Varroa* in particular. Only a few attempts of electrophysiological recordings from the *Varroa* foreleg have been mentioned in the literature.

Accordingly, there is a need for compounds that disrupt the *Varroa*-honey bee interaction by targeting *Varroa*'s olfactory system, and for methods of evaluating *Varroa*'s sensitivity to the compounds. Such compounds should confuse *Varroa* while minimally disrupting honey bee communication in the colony. The present disclosure seeks to fulfill these needs and provides further related advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, this disclosure features a method of treating *Varroa destructor* infection in a bee colony, including (A) providing a compound of Formula (I):

(I)

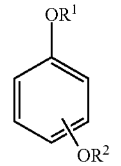

wherein $OR^2$ is an ortho, meta, or para substituent relative to $OR^1$, $R^1$ is selected from $C_{1-6}$ alkyl and $C_{2-6}$ alkenyl, and $R^2$ is selected from $C_{1-6}$ alkyl and $C_{2-6}$ alkenyl; and (B) placing the compound of Formula (I) in a bee colony enclosure.

In another aspect, this disclosure features a method of treating *Varroa destructor* infection in a bee colony, including (A) providing a compound of Formula (Ic):

(Ic)

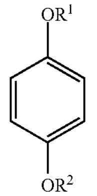

wherein $R^1$ is selected from $C_{1-6}$ alkyl and $C_{2-6}$ alkenyl, and $R^2$ is selected from $C_{1-6}$ alkyl and $C_{2-6}$ alkenyl; and (B) placing the compound of Formula (Ic) in a bee colony enclosure.

In another aspect, this disclosure features a method of treating *Varroa destructor* infection of a bee colony, including (A) providing a compound of Formula (II):

(II)

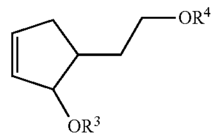

wherein $R^3$ is selected from $C_{1-6}$ alkyl and $C_{2-6}$ alkenyl, and $R^4$ is selected from $C_{1-6}$ alkyl and $C_{2-6}$ alkenyl; and (B) placing the compound of Formula (II) in a bee colony enclosure.

Embodiments can include one or more of the following features.

The methods can further include placing an acaricide in the bee colony enclosure; placing an organic acid in a bee colony enclosure; removing a drone brood comb from the bee colony enclosure after placing the compound of Formula (I), the compound of Formula (Ic), or the compound of Formula (II) in a bee colony enclosure; heat-treating a drone trapping comb after placing the compound of Formula (I), the compound of Formula (Ic), or the compound of Formula (II) in a bee colony enclosure; removing and heat-treating worker bees after placing the compound of Formula (I), the compound of Formula (Ic), or the compound of Formula (II) in a bee colony enclosure; confining a queen bee prior to, during, or after placing the compound of Formula (I), the compound of Formula (Ic), or the compound of Formula (II) in a bee colony enclosure; placing a sticky mite-trapping bottom board in a bee colony enclosure; transmitting *Varroa destructor* gene silencing dsRNA from the bee colony to *Varroa destructor*; placing a semiochemical such as *Varroa destructor* sex pheromone, DEET, nerolic acid, or any combination thereof into the bee colony enclosure; and/or selecting a bee colony such as a hygienic bee colony and/or a *Varroa destructor*-tolerant bee colony.

In some embodiments, placing a compound of the disclosure in a bee colony enclosure can inhibit electrophysiological responses of *Varroa destructor* to nurse bee headspace odor over a duration of 1 week or more and/or deter *Varroa destructor* from a nurse bee population in the bee colony.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 1A-1C shows the structures of embodiments of compounds of the present disclosure. FIG. 1A shows the structure of dialkoxybenzenes. FIG. 1B shows the structures of the 5(2'-methoxyethyl) cyclopent-2-en-1-alkoxy diethers (cy{$R_3$,1} compounds). And FIG. 1C shows the synthesis of the cy{$R_3$,1} compounds. Abbreviations: rt=room temperature; TBDMSCl=tert-butyl dimethylsilyl chloride; THF=tetrahydrofuran.

FIG. 4A-4C are bar graphs of the dose responses of examples of long-term inhibitory compounds cy{4,1}, 3b{2, 2} and cy{2,2}, specifically the responses of *Varroa* forelegs to stimulation with different amounts of each compound and with the headspace from 5 nurse bees (normalized values against the response to air %, average+SE). Bars within each dose, marked by different letters, are significantly different, ANOVA repeated measures, $p<0.05$, n=7.

FIG. 5A shows the effect of 0.1 μg cy{4,1} (left) or 3b{2,2} (right), with and without a simultaneous stimulus of the headspace volatiles from 5 nurse bees, on the electrophysiological response of the *Varroa* foreleg. The data are normalized values (%, average+SE): bars marked by different letters are significantly different, ANOVA repeated measures, $p<0.05$, $p<0.05$, n=6. FIG. 5B shows the longevity of the inhibitory effect of 0.1 μg of example compound cy{4,1} (left) or 0.1 μg (right) of example compound 3b{2,2} on *Varroa* foreleg electrophysiological responses. The time interval between the mixed stimulus (Bee+compound) and the pure bee stimulus was varied. Values are normalized against the response to air (%, average+SE): bars marked by different letters are significantly different, ANOVA Repeated Measures, $p<0.05$; n=6.

FIG. 6A is a graphical depiction of an experimental setup to study the effect of selected compounds on *Varroa* host choice between a nurse and a forager bee. FIG. 6B is a bar graph showing the effect of cy{4,1} on *Varroa* host choice: data are the percentage of *Varroa* that selected a particular host in the presence of hexane (control) or disrupting compound cy{4,1} at different doses (0.01 μg, 0.1 μg, 10 μg). Numbers within the bars show the number of *Varroa* choosing each of the hosts. FIG. 6C is a bar graph showing the effect of 3b{2,2} on *Varroa* host choice. FIG. 6D is a bar graph showing the effect of 3c{2,2} on *Varroa* host choice.

DETAILED DESCRIPTION

Figure 2B:
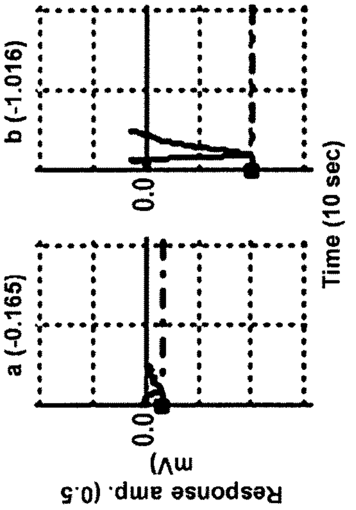
FIG. 2B are graphs showing examples of typical traces of *Varroa* foreleg response to air (left) and honey bee volatiles (right).

This disclosure presents compounds that affect the olfactory responses of *Varroa* and methods of use thereof. The compounds do not kill *Varroa*, and are therefore unlikely to generate *Varroa* resistance, compared to an acaricide. The compounds can work in conjunction with other mite control approaches, such as a bottom board excluder and sticky board control devices, and can enhance the performance of other forms of mite control while decreasing disadvantages associated therewith. Furthermore, the compounds of the present disclosure can be reproducibly synthesized, with little batch-to-batch variability. Thus, the availability of the compounds does not depend on a crop, such as hops or thyme, and is not influenced by natural product extraction procedures.

Compounds

The present disclosure provides, inter alia, a compound of Formula (I):

(I)

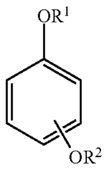

wherein:

$OR^2$ is a substituent on the phenyl at an ortho, meta, or para-position relative to $OR^1$;

$R^1$ is selected from $C_{1-6}$ alkyl and $C_{2-6}$ alkenyl, and $R^2$ is selected from $C_{1-6}$ alkyl and $C_{2-6}$ alkenyl.

In some embodiments, the compound of Formula (I) has Formula (Ia)

(Ia)

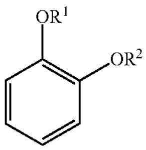

wherein:

$R^1$ is selected from $C_{1-6}$ alkyl and $C_{2-6}$ alkenyl, and $R^2$ is selected from $C_{1-6}$ alkyl and $C_{2-6}$ alkenyl.

In some embodiments, the compound of Formula (I) has Formula (Ib)

(Ib)

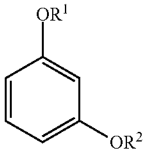

wherein:

$R^1$ is selected from $C_{1-6}$ alkyl and $C_{2-6}$ alkenyl, and $R^2$ is selected from $C_{1-6}$ alkyl and $C_{2-6}$ alkenyl.

In some embodiments, the compound of Formula (I) has Formula (Ic)

(Ic)

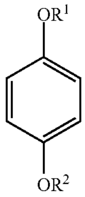

wherein:

$R^1$ is selected from $C_{1-6}$ alkyl and $C_{2-6}$ alkenyl, and $R^2$ is selected from $C_{1-6}$ alkyl and $C_{2-6}$ alkenyl.

In some embodiments, $R^1$ is selected from $C_{1-3}$ alkyl and $C_{2-3}$ alkenyl.

In some embodiments, $R^1$ is $C_{1-6}$ alkyl.

In some embodiments, $R^1$ is $C_{1-4}$ alkyl.

In some embodiments, $R^1$ is $C_{1-3}$ alkyl.

In some embodiments, $R^1$ is $C_{1-2}$ alkyl.

In some embodiments, $R^1$ is propyl.

In some embodiments, $R^1$ is methyl.

In some embodiments, $R^1$ is ethyl.

In some embodiments, $R^1$ is $C_{2-4}$ alkenyl.

In some embodiments, $R^1$ is $C_{2-3}$ alkenyl.

In some embodiments, $R^2$ is selected from $C_{1-3}$ alkyl and $C_{2-3}$ alkenyl.

In some embodiments, $R^2$ is $C_{1-6}$ alkyl.

In some embodiments, $R^2$ is $C_{1-4}$ alkyl.

In some embodiments, $R^2$ is $C_{1-3}$ alkyl.

In some embodiments, $R^2$ is $C_{1-2}$ alkyl.

In some embodiments, $R^2$ is methyl.

In some embodiments, $R^2$ is ethyl.

In some embodiments, $R^2$ is propyl (e.g., n-propyl).

In some embodiments, $R^1$ is $C_{2-4}$ alkenyl.

In some embodiments, $R^2$ is $C_{2-3}$ alkenyl.

In some embodiments, $R^1$ is selected from $C_{1-3}$ alkyl and $C_{2-4}$ alkenyl, and $R^2$ is selected from $C_{1-3}$ alkyl and $C_{2-4}$ alkenyl.

In some embodiments, $R^1$ is selected from $C_{1-3}$ alkyl and $C_{2-3}$ alkenyl, and $R^2$ is selected from $C_{1-3}$ alkyl and $C_{2-3}$ alkenyl.

In some embodiments, $R^1$ is $C_{1-3}$ alkyl and $R^2$ is $C_{1-3}$ alkyl.

In some embodiments, $R^1$ is $C_{1-3}$ alkyl and $R^2$ is $C_{1-2}$ alkyl.

In some embodiments, $R^1$ is $C_{1-2}$ alkyl and $R^2$ is $C_{1-3}$ alkyl.

In some embodiments, $R^1$ is $C_{1-2}$ alkyl and $R^2$ is $C_{1-2}$ alkyl.

The present disclosure also provides, inter alia, a compound of Formula (II):

(II)

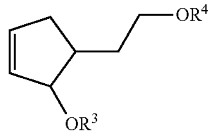

wherein:

$R^3$ is selected from $C_{1-6}$ alkyl and $C_{2-6}$ alkenyl; and $R^4$ is selected from $C_{1-6}$ alkyl and $C_{2-6}$ alkenyl.

In some embodiments, $R^3$ is $C_{1-6}$ alkyl.

In some embodiments, $R^3$ is $C_{1-5}$ alkyl.

In some embodiments, $R^3$ is $C_{1-4}$ alkyl.

In some embodiments, $R^3$ is $C_{1-3}$ alkyl.

In some embodiments, $R^3$ is methyl.

In some embodiments, $R^3$ is ethyl.

In some embodiments, $R^3$ is propyl (e.g., n-propyl).

In some embodiments, $R^3$ is butyl (e.g., n-butyl).

In some embodiments, $R^3$ is pentyl (e.g., n-pentyl).

In some embodiments, $R^3$ is $C_{2-4}$ alkenyl.

In some embodiments, $R^3$ is $C_{2-3}$ alkenyl.

In some embodiments, $R^4$ is $C_{1-6}$ alkyl.

In some embodiments, $R^4$ is $C_{1-4}$ alkyl.

In some embodiments, $R^4$ is $C_{1-3}$ alkyl.

In some embodiments, $R^4$ is $C_{1-2}$ alkyl.

In some embodiments, $R^4$ is methyl.

In some embodiments, $R^4$ is ethyl.

In some embodiments, $R^4$ is $C_{2-4}$ alkenyl.

In some embodiments, $R^4$ is $C_{2-3}$ alkenyl.

In some embodiments, $R^3$ is $C_{1-5}$ alkyl and $C_{2-4}$ alkenyl and $R^4$ is selected from $C_{1-3}$ alkyl and $C_{2-4}$ alkenyl.

In some embodiments, $R^3$ is $C_{1-5}$ alkyl and $C_{2-3}$ alkenyl and $R^4$ is selected from $C_{1-3}$ alkyl and $C_{2-3}$ alkenyl.

In some embodiments, $R^3$ is $C_{1-5}$ alkyl and $R^4$ is $C_{1-3}$ alkyl.

In some embodiments, $R^3$ is $C_{1-5}$ alkyl and $R^4$ is $C_{1-2}$ alkyl.

In some embodiments, $R^3$ is $C_{1-3}$ alkyl and $R^4$ is $C_{1-3}$ alkyl.

In some embodiments, $R^3$ is $C_{1-3}$ alkyl and $R^4$ is $C_{1-2}$ alkyl.

In some embodiments, the compounds of Formula (II) have cis-substituents on the cyclopentene ring and are racemic. For example, the compounds of Formula (II) can have formula (IIa) or (IIb):

(IIa)

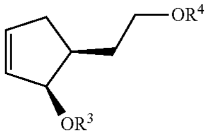

(IIb)

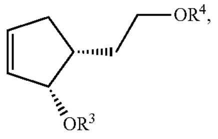

wherein $R^3$ and $R^4$ are as defined above.

In some embodiments, the compound of Formula (I) is selected from

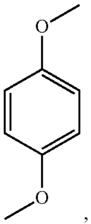,
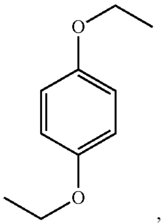,
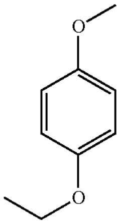,
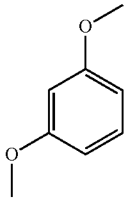,
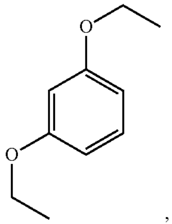, and
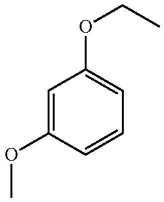.

In some embodiments, the compound of Formula (II) is selected from

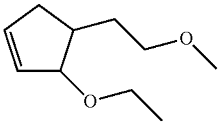,
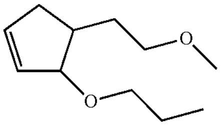,
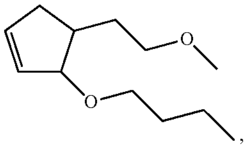, and
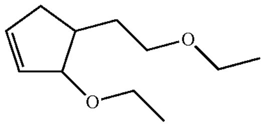.

The alkoxy substituents on the cyclopentene ring can be cis relative to one another.

In some embodiments, the compounds of the invention is enantiomerically enriched, in that a given mixture of compounds of Formulas (IIa) and (IIb) can have an enantiomeric excess of a compound of Formula (IIa), or a compound of Formula (IIb), wherein $R^3$ and $R^4$ are as defined above. The enantiomeric excess can range, for example, from 0% (i.e., racemic) to 99% (e.g., from 0% to 80%, from 0% to 60%, from 0% to 40%, from 0% to 20%, from 0% to 10%).

Figure 2C:
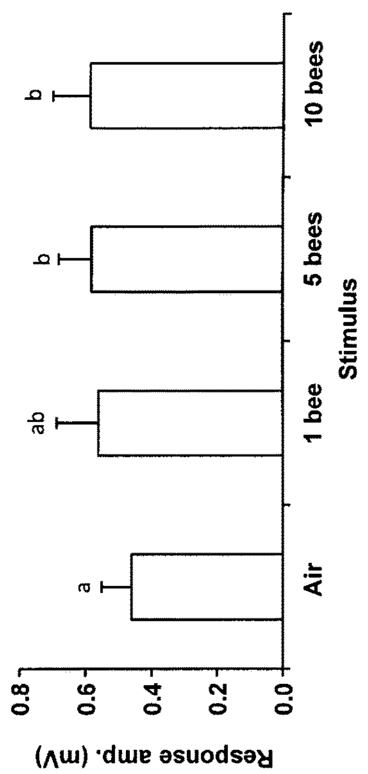
FIG. 2C is a bar graph showing *Varroa* foreleg electrophysiological response amplitude. From left to right, the bars indicate the *Varroa* responses to the headspaces of different numbers of bees: no bee (empty jar), 1 bee, 5 bees, and 10 bees. ANOVA (Analysis of Variance) repeated measures: bars marked by different letters are significantly different, $p<0.05$, $n=6$.
Figure 2A:
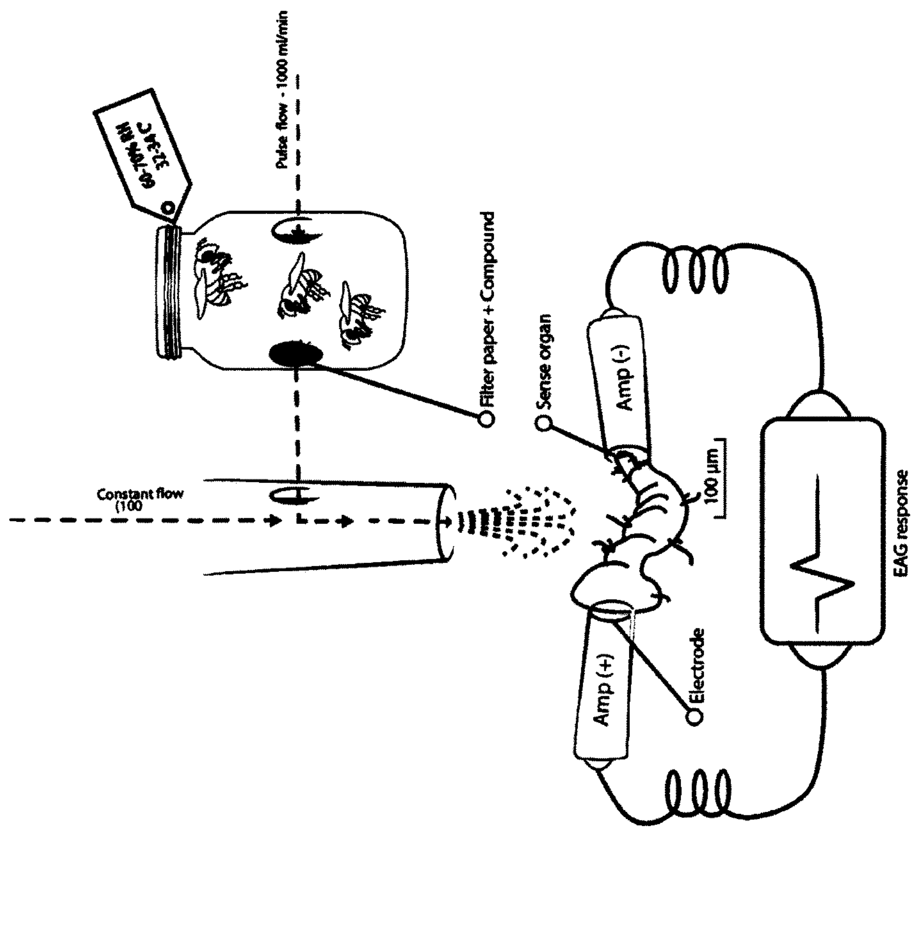
FIG. 2A is a graphical depiction of an example of an electrophysiology setup of an isolated *Varroa* foreleg that was stimulated with the headspace volatiles of freshly caught honey bees in a jar.
Figure 6A:
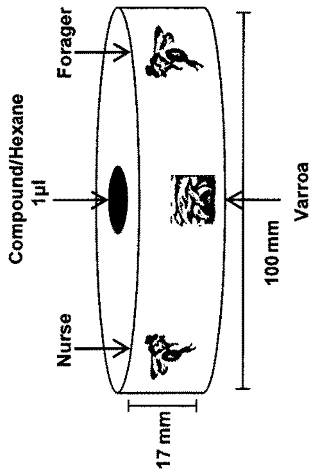
FIGS. 6A-6D are graphical representations and bar graphs showing the effect of embodiments of the compounds of the present disclosure on *Varroa* host choice between a nurse and a forager bee.

In some embodiments, the compounds of the present disclosure are effective in disrupting *Varroa*'s olfactory response to honey bee headspace. The *Varroa* olfactory response, including sensitivity, can be monitored by measuring electrophysiological responses of *Varroa* to nurse bee headspace odor, as illustrated in FIG. 2A and as further described in Example 1, below. In some embodiments, the *Varroa*'s preference for nurse bees and for brood cells can be deterred in the presence of the compounds of the present disclosure. Thus, the compounds of the present disclosure can deter *Varroa* from a nurse bee population and from brood cells. The preference of *Varroa* for a nurse bee or a forager bee in the presence of the compounds of the present disclosure can be evaluated using an experimental bioassay setup as illustrated in FIG. 6A and as further described in Example 1, below.

Definitions

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further intended that the compounds of the disclosure are stable. As used herein "stable" refers to a compound that is sufficiently robust to survive isolation to a useful degree of purity from a reaction mixture.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

"Optionally substituted" groups can refer to, for example, functional groups that may be substituted or unsubstituted by additional functional groups. For example, when a group is unsubstituted, it can be referred to as the group name, for example alkyl or aryl. When a group is substituted with additional functional groups, it may more generically be referred to as substituted alkyl or substituted aryl.

As used herein, the term "alkyl" is meant to refer to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. For example, an alkyl group can contain from 1 to about 10, from 1 to about 8, from 1 to about 6, from 1 to about 4, or from 1 to about 3 carbon atoms.

As used herein, the term "alkylene" refers to a linking alkyl group.

As used herein, "alkenyl" refers to an alkyl group having one or more double carbon-carbon bonds. The alkenyl group can be linear or branched. Example alkenyl groups include ethenyl, propenyl, and the like. For example, an alkenyl group can contain from 2 to about 10, from 2 to about 8, from 2 to about 6, or from 2 to about 4 carbon atoms.

As used herein, "alkenylene" refers to a linking alkenyl group.

As used herein, "alkoxy" refers to an —O-alkyl group. Example alkoxy groups include methoxy, ethoxy, propoxy (e.g., n-propoxy and isopropoxy), t-butoxy, and the like.

As used herein, "enantiomeric excess" refers to the degree to which a sample contains one enantiomenr in greater amounts than the other. For example, a racemic mixture has an enantiomeric excess of 5%. A pure enantiomer has an enantiomeric excess of 100%. A sample with 80% of one enantiomer and 20% of another enantiomer has an enantiomeric excess of 60%.

Compounds of the present disclosure that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins and the like can also be present in the compounds described herein, and all such stable isomers are contemplated in the present disclosure.

Compounds of the disclosure can also include all isotopes of atoms occurring in the intermediates or final compounds.

Isotopes include those atoms having the same atomic number but different mass numbers. For example, isotopes of hydrogen include tritium and deuterium.

In some embodiments, the compounds of the disclosure, and salts thereof, are substantially isolated. By "substantially isolated" is meant that the compound is at least partially or substantially separated from the environment in which it was formed or detected. Partial separation can include, for example, a composition enriched in the compound of the disclosure. Substantial separation can include compositions containing at least about 50%, at least about 60%, at least about 70%, at least about 80%, at least about 90%, at least about 95%, at least about 97%, or at least about 99% by weight of the compound of the disclosure, or salt thereof. Methods for isolating compounds and their salts are routine in the art.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Synthesis

The compounds of the present disclosure can be prepared in a variety of ways known to one skilled in the art of organic synthesis. The compounds of the present disclosure can be synthesized using the methods as described below and in Example 1, together with synthetic methods known in the art of synthetic organic chemistry or variations thereon as appreciated by those skilled in the art.

Compounds of the present disclosure, such as substituted alkoxy benzenes, can be synthesized as described, for example, in Paduraru et al., J. Comb. Chem 10: 123-134. Substituted cyclopentenes can be synthesized, as described, for example, in Chen et al., (2010) Bioorg Med Chem 18: 2920-2929 and Chen H., Plettner E., (2012) Tetrahedron Letters 53: 2059-2062.

FIG. 1C provides a general synthetic scheme for the preparation of embodiments of the compounds of Formula (II). Referring to FIG. 1C, diol 1 can be singly protected by reaction with tert-butyldimethylsilyl chloride (TBDMSCl) and imidazole in dichloromethane. The monoprotected diol 2 can be reacted with potassium metal in tetrahydrofuran (THF), followed by addition of the appropriate alkyl bromide or iodide ($R_3Br$ or $R_3I$), resulting in compound 3. This intermediate was deprotected using tetrabutylammonium fluoride (TBAF) in THF, to give compound 4. This compound was reacted with potassium in THF, followed by iodomethane, to give the final product.

The compounds of this disclosure can be prepared from readily available starting materials. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^{1}H$ or $^{13}C$) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 4th. Ed., Wiley & Sons, 2006.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art. As another example, an esterase reaction can be used to resolve a precursor compound (e.g., a diol, such as compound 1 in FIG. 1C), as described, for example, in Chen, H. et al., Tetrahedron Asymmetry, 2009, 20, 449-456.

Formulations

In some embodiments, one or more compounds of the present disclosure can be combined with one or more carriers, antioxidants, and/or preservatives to provide a formulation. The formulation can be in the form of a liquid, paste, solid, or gel. In some embodiments, the formulation is a controlled release formulation, such that the compounds can be released (i.e., volatilized) over a period of time. Exemplary carriers include oils; polymers (e.g., polyethylene glycol, polymethacrylates, ethylene-vinyl acetate copolymers, poly(acrylic acid), polyolefins (e.g., polypropylene), silicones, lactic and glycolic acid-based polymers, and copolymers thereof); microcapsules (e.g., silica microcapsules); glasses; gels; ceramics; and waxes.

Exemplary oils to use with the one or more compounds of the present disclosure include, but are not limited to, oils derived from plants such as vegetable oils and nut oils, or non-plant derived oils such as mineral oils. The oils include saturated, monounsaturated, and polyunsaturated fatty acids that are soluble in many compositions, especially the less polar or non-polar ones.

Exemplary preservatives include, for example, sorbic acid and its salts, benzoic acid and its salts, calcium propionate, sodium nitrite, sulfites (sulfur dioxide, sodium bisulfite, potassium hydrogen sulfite, etc.) and disodium ethylenediaminetetraacetic acid (EDTA). Other exemplary preservatives include ethanol and methylchloroisothiazolinone, salt, sugar, vinegar, alcohol, diatomaceous earth and castor oil, citric and ascorbic acids, vitamin C, and vitamin E.

Exemplary antioxidants include, but are not limited to, tocopherols (e.g., I-tocopherol, γ-tocopherol, etc.), ascorbic acid, as well as synthetic antioxidants such as propyl gallate, tertiary butylhydroquinone, butylated hydroxytoluene (BHT), butylated hydroxyanisole (BHA), phenolic alcohols, flavonoids, catechins, related molecules thereof, and anthocyanins and their glycosides. The antioxidants can be soluble in most of the compositions and can react efficiently with oxygen in the dispensing systems, and therefore offer a way to decrease oxidation, breakdown, and polymerization of the formulation. In some embodiments, the oxidant can also be a preservative.

While representative carriers, preservatives, and antioxidants have been listed above, it is to be appreciated that other carriers, preservatives, and antioxidants not specifically listed above can also be used.

In some embodiments, the formulation is a controlled release formulation, such that the one or more compounds of the present disclosure contained therein can slowly release over an extended period of time (e.g., between 1 and 4 weeks, between 1 and 3 weeks, or between 1 and 2 weeks; about 1 week, about 2 weeks, about 3 weeks, or about 4 weeks). The formulation can be contained in a dispenser (e.g., a bag, a perforated tube, or an open container) that is permeable to the one or more compounds of the present disclosure. In some embodiments, the dispenser is formed of plastic, paper, wax, and/or wood.

Methods of Use

The compounds and formulations described above can be used to treat (i.e., reduce or eliminate) *Varroa* infections in a honey bee colony, when placed inside a bee colony enclosure.

Bee Colony Enclosure

The bee colony enclosure can be any kind of an enclosed structure in which the bee colony lives and raise its young. The bee colony enclosure's internal structure can include a densely packed group of hexagonal cells, made of beeswax (i.e., a honeycomb, or a comb). The cells are used to store food (e.g., honey and pollen) and to house the brood (i.e., eggs, larvae, and pupae).

In some embodiments, the bee colony enclosure can be a naturally occurring structure occupied by bee colonies, such as hollowed-out trees. In some embodiments, the bee colony can be domestic and live in man-made beehives, which can be in an apiary. As an example, a man-made beehive can include the following parts:

(1) A hive stand on which upper hive components rest. The hive stand provides a landing board for the bees and helps to protect the bottom board from rot and cold transfer.
(2) A bottom board having an entrance for the bees to get into the hive.
(3) One or more brood boxes. The one or more brood boxes are typically the low box(es) of the hive and are where the queen bee lays her eggs. Each brood box includes brood combs, which are the beeswax structures of hexagonal cells where the queen bee lays eggs (i.e., the brood cells).
(4) Honey super box(es), which are usually shorter than the brood box, but are the uppermost box(es) where honey is stored in honeycombs. The honeycombs are the beeswax structure of hexagonal cells where the honey is stored.
(5) Frames and foundation, which are wooden or plastic frames with wax or plastic sheets with honeycomb impression where bees build wax honey combs.
(6) An inner cover, which provides separation from an overly hot or cold outer cover and can be used as a shelf for feeding or other purposes.
(7) An outer cover, which provides weather protection for the hive.

*Varroa* Treatment

The compounds and formulations of the present disclosure can be used alone, or with one or more additional *Varroa* control methods, to treat *Varroa* infection in a bee colony.

The compounds and formulations can be applied generally to a bee colony enclosure, or to a specific portion of a bee colony enclosure. In some embodiments, the compounds and formulations are applied to a brood area, such as one or more brood cells, or to a brood box, to provide focused and localized deterrence of *Varroa* host attraction to brood cells and to disrupt the *Varroa*'s olfactory response to nurse bees, which are present in greater numbers in the brood box.

The compounds (or formulations) can be provided in a release device, which can slowly release the compounds over a period of time. Examples of release devices include strips (e.g., a compound-impregnated strip made of, for example, paper or coated paper) or other means that are easy to install, monitor and replace. In some embodiments, the compounds or formulations can be dispensed within a bee colony enclosure with an evaporator, as a spray, from a pad, or as a drizzle. In certain embodiments, the compounds or formulations are dispensed within a bee colony enclosure with a pad. In some embodiments, the release device containing the compounds (or formulation) is installed in a space that is between brood combs. In some embodiments, when the release device is a strip, the strips are designed fit over the top of the frames in bee colony enclosure. If the release device is installed in and/or around the brood nest area and the neighboring areas, then emerging *Varroa* will be exposed to the compound.

The compounds of the present disclosure can be released in an amount that is at least 300 μg/volume between brood combs/month (e.g., at least 400 μg/volume between brood combs/month, at least 500 μg/volume between brood combs/month, or at least 600 μg/volume between brood combs/month). When released into the bee colony enclosure or a portion of the bee colony enclosure (e.g., the brood box), the compounds of the present disclosure can inhibit electrophysiological responses (i.e., the olfactory response) of *Varroa* to nurse bee headspace odor over a duration of 1 week or more (e.g., 2 weeks or more, 3 weeks or more, or 4 weeks or more).

In some embodiments, in addition to using the compounds (or formulations) of the present disclosure, one or more other *Varroa* infection control methods are also used. Examples of other *Varroa* infection control methods include acaricides, organic acids, biotechnical control methods, bee breeding, RNA interference control methods, *Varroa* parasite control methods, *Varroa* predator control methods, and semiochemical control methods, each of which can be used singly or in any combination with the compounds (or formulations) of the present disclosure.

The use of the present compounds (or formulations) with other infection control methods can include numerous advantages, such as (1) ameliorating the various drawbacks associated with these infection control methods; (2) allowing the different *Varroa* infection control methods to work in a synergistic manner, such that the *Varroa* population decrease with the use of two or more methods is more than the additive decrease of each method, when used alone; and (3) decreasing the likelihood that drone, queen, or worker bees would be killed even as *Varroa* is being controlled. Examples of *Varroa* control using the compounds (or formulations) of the present disclosure and one or more other infection control methods are provided below.

In some embodiments, the compounds of the present disclosure are used concurrently with an acaricide in the bee colony enclosure. Without wishing to be bound by theory, it is believed that while acaricides can be highly effective for decreasing *Varroa* population, they are subject to the development of resistance, can cause bee mortality, can cause sub-lethal effects in bees, can cause irritation in bee populations, and/or can affect the quality and taste of honey due to contamination of the honey by the acaricide. In some cases, *Varroa* control levels can be variable. The compounds of the present disclosure can mitigate any unintentional toxicity and increase the effectiveness of the acaricide to bee brood by directing *Varroa* away from brood cells so that they can be targeted by the acaricide that is located elsewhere in the bee colony enclosure. For example, the compounds of the present disclosure can be placed in the brood box and deter *Varroa* from brood cells, so that *Varroa* can come into contact with an acaricide that is placed at least 10 cm (e.g., at least 20 cm, or at least 30 cm) above or next to the outermost frames of the brood box. In some embodiments, the acaricide is placed at least one frame height (e.g., about 30 cm) above or next to the outermost frames of the brood box (about 10-15 cm). The compounds of the present disclosure can also decrease the likelihood of resistance development, when used as part of an integrated resistance management ("IRM") scheme, wherein different control methods are used in subsequent years in conjunction with acaricides. In some embodiments, acaricides can be used as part of an integrated resistance management treatment plan, provided that the Varro is not completely resistance to the acaricide. In some embodiments, the compounds of the present disclosure can decrease the amount of acaricide that is needed for effective *Varroa* control, thereby decreasing irritation that can occur in bee population due to the presence of the acaricide; and/or increasing the quality and taste of honey extracted from the bee colony enclosure by decreasing the likelihood of acaricide contamination of the honey.

In some embodiments, the acaricide is placed at least 10 cm (e.g., at least 20 cm, at least 30 cm, at least 40 cm) from brood cells in a bee colony enclosure. Examples of acaricides include a pyrethroid, a formamidine, and an organophosphate. In some embodiments, the acaricide is thymol, eucalyptol, camphor, menthol, methyl salicylate, or any combination thereof. In some embodiments, the acaricide can be a plant extract, such as an essential oil. Non-limiting examples of plant extracts include citronella oil, geranium oil, lavender oil, clove oil, *Eupatorium buniifolium* leaf extract, lupulones, hops extract, laurel leaf extract, 1,8-cineole, marjoram extract, mint oil, neem oil, oregano oil, and wintergreen oil.

As an example, neem oil is acaricidal but is also toxic to bee brood and to the queen. Therefore, it cannot be used in the brood nest. By releasing the compounds of the present disclosure (e.g., from a release device) near the brood cells and applying neem oil away from the brood cells, *Varroa* can be moved away from the brood nest to the periphery where older bees reside and where neem oil is present. The negative effects of neem oil can thus be mitigated, while taking advantage of its acaricidal effect.

As another example, the volatile compound thymol, which can be formulated into tablets or gels, is acaricidal. However, thymol is a strong irritant to the bees. By placing the compounds of the present disclosure to the brood cells and applying thymol away from the brood cells, phoretic *Varroa* can be moved away from the brood nest. Thus, the negative effects of thymol on bees can be mitigated while the acaricidal benefits of thymol can be preserved. Other acaricides can be used in conjunction with the compounds of the present disclosure in an analogous manner.

In some embodiments, the compounds of the present disclosure are used concurrently with an organic acid in the bee colony enclosure. Without wishing to be bound by theory, it is believed that while organic acids are effective in killing hive microflora through a fumigant effect, high concentrations of organic acids can be toxic to bee colonies. The compounds of the present disclosure can mitigate disadvantages to bee populations and/or enhance the effectiveness of the organic acid for *Varroa* control by directing *Varroa* away from brood cells so that they can be targeted by an organic acid that is located elsewhere in the bee colony enclosure. In some embodiments, a smaller amount of an organic acid is required for effective *Varroa* control in the presence of the compounds of the present disclosure. For example, the compounds of the present disclosure can be placed in the brood box and deter *Varroa* from the brood cells within the brood box, so that *Varroa* can come into contact with an organic acid that is placed outside of the brood box in a bee colony enclosure. Examples of organic acids include formic acid, oxalic acid, lactic acid, and ascorbic acid.

As an example, the volatile compound formic acid kills phoretic *Varroa*. However, formic acid also causes bee mortality. By releasing the compounds of the present disclosure near the brood cells and applying formic acid (e.g., in the form of a pad impregnated with formic acid) away from the brood cells, *Varroa* can be moved away from the brood cells and to a periphery where older bees reside and where the formic acid is located. The negative effects of formic acid can thus be mitigated, while taking advantage of its ability to kill phoretic *Varroa*.

As another example, oxalic acid vapors (dispensed either with an evaporator, as a spray, from a pad or as a drizzle) can kill phoretic *Varroa*. When used together with the compounds of the present disclosure, the compounds can prolong phoretic timing by moving *Varroa* from nurse bees (which can bring the mites to new brood cells where they reproduce) to foragers (which take mites away from the brood nest). Thus, a greater number of *Varroa* can be killed in the presence of the compounds of the present disclosure, compared to treatment without the compounds of the present disclosure.

In some embodiments, ascorbic acid can be used to improve immune responses in bees, when fed to bees in sugar syrup. When used in combination with the compounds of the present disclosure, the overall health of the bee colony can improve as *Varroa* is deterred from the brood cells and the bees acquire stronger immune responses against *Varroa*.

In some embodiments, the compounds of the present disclosure are used concurrently with biotechnical control methods. However, biotechnical control methods may not be effective for treating *Varroa* at certain periods of its life cycle, and may be disruptive to the colony, labor intensive, and can be stressful to the bee colony (e.g., the brood, queen, workers, or drone). The compounds of the present disclosure can enhance the effectiveness of the biotechnical control methods for *Varroa* control by directing *Varroa* away from brood cells to other areas in the bee colony enclosure, by prolonging *Varroa* phoretic period, and can result in less disruption and stress to the colony due to increased effectiveness of the combined control methods. For example, the compounds of the present disclosure, when placed near worker brood cells, can deter *Varroa* from the worker brood cells, so that *Varroa* can directed and concentrated to other areas of the bee colony enclosure, which can in turn be subjected to biotechnical methods.

Examples of biotechnical methods include drone brood comb removal, heat treatment of drone trapping comb, heat treatment of workers (removed from broodless colonies in the fall), queen confinement, and use of a sticky bottom board in a bee colony enclosure.

As an example, drone brood comb removal can be used to remove many reproducing *Varroa* and their brood from the bee colony. This method makes use of the 10-12 time preference of the *Varroa* for drone cells over worker cells for reproduction, by inserting drone trapping combs into the bee colony enclosure and removing the drone trapping combs when the drone brood has been sealed inside the cells (about 20 days after insertion of the trapping combs into the bee colony enclosure). While drone comb removal is effective in removing a large number of reproducing *Varroa* and their brood from the colony, it is not very effective in treating phoretic *Varroa*, nor for addressing reproducing *Varroa* in worker cells. By concurrently applying the compounds of the present disclosure to worker brood cells, *Varroa* can be directed away from worker brood cells and can be concentrated in, for example, the drone trapping comb, which can be removed. Thus, *Varroa* control using drone brood comb removal can be rendered more effective through use of the compounds of the present disclosure.

In some embodiments, rather than removing a drone trapping comb, *Varroa* can be killed in the drone trapping comb by heating the drone trapping comb using a comb heater, which is selectively embedded into a drone trapping comb.

As another example, in addition to using the compounds of the present disclosure, the queen bee can be temporarily confined on a *Varroa* trapping comb. The queen can be confined for one generation of worker bee brood. When existing worker brood has emerged, only phoretic *Varroa* exist, which can be controlled using methods that target phoretic *Varroa* (e.g., oxalic acid). The compounds of the present disclosure can cause phoretic *Varroa* emerging from existing brood or the trap comb to move towards forager bees, so that any phoretic *Varroa* control method can be concentrated in the brood nest periphery, thereby enhancing the effectiveness of the phoretic *Varroa* control method.

As yet another example, a *Varroa* control method can include using the compounds of the present disclosure to deter *Varroa* from the brood cells and direct *Varroa* toward worker bees, which can then be removed and heat treated to kill the *Varroa* on their bodies (*Varroa* are killed at temperatures of 40-48° C., but bees can survive the treatment). The compounds of the present disclosure can thus enhance the effectiveness of worker bee heat treatment as a *Varroa* control method.

As another example, the compounds of the present disclosure can enhance *Varroa* control when used together with a sticky mite-trapping bottom board in a bee colony enclosure. The compounds of the present disclosure can be placed near brood cells and deter *Varroa* from the brood cells. As the *Varroa* travels through the bee colony enclosure, they can fall onto and be trapped by the sticky bottom board.

In some embodiments, the compounds of the present disclosure are used concurrently with bee breeding methods for *Varroa* control. Examples of breeding methods include the use of hygienic bee lines and *Varroa* tolerant bee lines. The compounds of the present disclosure can enhance the effectiveness of the bee breeding methods in decreasing *Varroa* population. For example, hygienic bee lines that are bred to more actively remove diseased brood can be used in conjunction with the compounds of the present disclosure to better control *Varroa* population. As another example, *Varroa* tolerant bee lines can be used together with the compounds of the present disclosure to ensure long-term health of the bee colony.

In some embodiments, the compounds of the present disclosure are used concurrently with RNA interference methods for *Varroa* control. For example, bees can be fed with specific double-stranded RNA that is then transmitted to *Varroa*, which has the potential of weakening *Varroa* and decreasing *Varroa* population. In some embodiments, rather than infecting *Varroa* directly, bees can be inoculated with deformed wing virus-specific double-stranded RNA to strengthen the bees against wing virus infection, which are vectored by the *Varroa*. The *Varroa*-targeted RNA can be fed to bees that vector the nucleic acid to the *Varroa*. In some embodiments, the RNA feeders are placed in the periphery of the nest and are ingested by bee foragers. By using the compounds of the present disclosure, *Varroa* can be directed to move towards forager bees, thus ensuring better vectoring of the RNA from the forager bees to the *Varroa*.

In some embodiments, the compounds of the present disclosure are used in conjunction with a semiochemical that is different from the present compounds. The semiochemicals can have a variety of effects. For example, the semiochemicals can disrupt mating behavior, halt reproduction, shift *Varroa* preference for nurse bee host to forager bees, remove *Varroa* from brood cells, repel *Varroa*, attract *Varroa*, and/or arrest *Varroa*'s search for brood cells. However, the semiochemicals can cause confusion to the bees if they are also used in bee communication. By using compounds of the present disclosure, less of the other semiochemicals may be used, thereby causing less disruption to the bee colony.

Examples of semiochemicals can include *Varroa* sex pheromones (e.g., a blend of oleic, palmitic, and stearic acids, and minor quantities of their respective ethyl esters), *Varroa* reproductive stop signal (e.g., a blend of fatty acid methyl esters: methyl palmitate, methyl oleate, methyl stearate, methyl linoleate and methyl linolenate), DEET, nerolic acid. In some embodiments, the semiochemical is a kairomone, which is a semiochemical emitted by an organism that mediates interspecific interactions in a way that benefits an individual of another species which receives it, without benefitting the emitter.

As an example, the brood kairomone of the bees that signals the right timing for reproduction to *Varroa* has been used to induce reproductively-ready female mites (i.e., *Varroa* foundresses) to skip one reproductive cycle, even while in a cell with a bee pupa. Therefore, the bee brood kairomone, in conjunction with the compounds of the present disclosure can lower reproduction rates, because the female foundresses re-emerge with the bee, regardless of whether they have reproduced. The compounds of the present disclosure can thus work synergistically with the brood kairomone: the kairomone disrupts the timing of *Varroa* egg laying, while the compounds of the present disclosure is effective on *Varroa*'s phoretic stage.

As another example, the *Varroa* pheromone can be used in conjunction with the compounds of the present disclosure. In the absence of the *Varroa* pheromone, the male *Varroa* mates only with the young, newly emerged, female *Varroa*. Adding the *Varroa* pheromone can disrupt the mate-selection process by promoting male *Varroa* to unsuccessfully mate with *Varroa* foundresses or older females. The compounds of the present disclosure can further direct *Varroa* away from brood cells, thereby further decreasing the *Varroa* population.

As yet another example, the semiochemical can be an arrestant, which is a semiochemical that stops movement in *Varroa*. The arrestant can be dispensed with an acaricide in the nest periphery, while the compounds of the present disclosure can be released near brood cells. The compounds of the present disclosure can work synergistically with the arrestant and acaricide by deterring *Varroa* from brood cells and directing *Varroa* toward forager bees at the periphery, where the arrestant and acaricide can stop and kill the *Varroa*.

While compounds of the disclosure are described above as being used in conjunction with one additional *Varroa* control method above, such as an acaricide, an organic acid, a biotechnical method, bee breeding control methods, RNA interference, *Varroa* parasites, *Varroa* predators, or semiochemicals, it is understood that the compounds can be used in conjunction with two or more *Varroa* control methods described herein, in any combination.

The Example below describes *Varroa*-disruptive compounds and methods of using these compounds. In the presence of some compounds, the response of the *Varroa* chemosensory organ to honey bee headspace volatiles significantly decreased. This effect was dose dependent and can be long lasting (>1 min). Furthermore, disruption of the *Varroa* volatile detection was accompanied by a reversal of *Varroa*'s preference from a nurse to a forager bee. Long-term inhibition of the electrophysiological responses of mites to the tested compounds was a good predictor for an alteration in the mite's host preference.

EXAMPLES

The general location of the olfactory organ differs in mites and insects. In honey bees, like in all insects, the antennae are the major olfactory organ, whereas mites lack antennae and, therefore, the olfactory organ of the *Varroa* is located on the distal part of its forelegs, analogous to the sensory pit (Haller's organ) found in ticks. Although chemosensory sensilla in the mite's sensory pit appear similar to those described in insects, not much is known about the mechanism behind odorant detection in mites in general and *Varroa* in particular. Only a few attempts of electrophysiological recordings from the *Varroa* foreleg have been mentioned in the literature. Furthermore, the response of the organ to honeybee volatiles had not been previously confirmed. In the present Example measurement of the response of the *Varroa* foreleg to host (honeybee) volatiles is established. The effect of the potentially disruptive compounds (e.g., ethers of 5(2'-hydroxyethyl) cyclopent-2-en-1-ol or of dihydroquinone, resorcinol or catechol) on this response, as well as on *Varroa*'s ability to distinguish between two host types (a nurse and a forager bee) was also evaluated.

Two methods were implemented to assess the effect of potential disrupting compounds: (1) electrophysiology was used to assess the effect of the compounds on the sensitivity of the *Varroa* chemosensory organ to honey bee volatiles; and (2) the ability of compounds alter the *Varroa*'s preference for a nurse over a forager bee was also examined using a behavioral bioassay.

Biological Material

Honey bee colonies (*A. mellifera liguistica*) were maintained at an experimental apiary at Bet Dagan, ARO the Volcani Center, Israel. The experimental hives were maintained without any treatment against *Varroa*, but received seasonal sugar feeding and Fumagilin treatment against *Nosema*.

Female adult *Varroa* mites were collected from a tray under a screen net at the bottom of the hive, and were kept on a moisture filter paper at room temperature up to 4 hours prior to the experiments. Adult honey bees of two task groups (nurse and foragers) were collected for the experiments. Honeybees observed leaning into brood cells were regarded as nurse bees whereas pollen foragers, carrying pollen loads, were collected from the entrance of the hive according to Kather et al., (2011) J. Chem. Ecol. 37: 205-212. The bees were killed by freezing at −20° C., for 1 hour. Prior to a behavioral bioassay, the pollen loads were thoroughly removed from forager bees by using forceps under stereo microscope (Olympus DF PLAPO 1XPF JAPAN). Nurses were used as taken from the hive.

Chemical Compound Synthesis

The compounds tested included four para-dialkoxybenzenes (FIG. 1A), a 5-compound library of dialkyl ethers of cis 5-(T-hydroxyethyl)cyclopent-2-en-1-ol (cy{1-5,1} code HC 2-169) and the individual library members (FIG. 1B).

The compounds were synthesized as described in Paduraru et al., J. Comb. Chem 10: 123-134, whereas the alicyclic ethers were synthesized as described in Chen et al., (2010) Bioorg Med Chem 18: 2920-2929, and Chen H., Plettner E., (2012) Tetrahedron Letters 53: 2059-2062.

Synthetic Procedures and Spectroscopic Data of the Racemic cy{$R_3$,1} Compounds FIG. 1C provides a general synthetic scheme for the preparation of the cy{$R_3$,1} compounds. Referring to FIG. 1C, diol 1 was singly protected by reaction with tert-butyldimethylsilyl chloride (TBDMSCl) and imidazole in dichloromethane. The monoprotected diol 2 was reacted with potassium metal in tetrahydrofuran (THF), followed by addition of the appropriate alkyl bromide or iodide ($R_3Br$ or $R_3I$), resulting in compound 3. This intermediate was deprotected using tetrabutylammonium fluoride (TBAF) in THF, to give compound 4. This compound was reacted with potassium in THF, followed by iodomethane, to give the final product cy{$R_3$,1}.

Synthesis of (±)-cis-5-[2-(tert-Butyl-dimethyl-silanyloxy)-ethyl]cyclo-pent-2-enol 2

A solution of compound 1 (1.5 g, 11.7 mmol), triethylamine (1.42 g, 14.0 mmol), DMAP (142 mg, 1.17 mmol), tert-butyldimethylsilyl chloride (2.11 g, 14.0 mmol) in $CH_2Cl_2$ was stirred at 0° C. for 12 h. The reaction mixture was diluted with $CH_2Cl_2$ and washed with water and brine. The organic layer was dried over $MgSO_4$ filtered and concentrated under vacuum. The crude product was purified by flash chromatography on silica gel (EtOAc/hexane 3:7) to afford pure alcohol 2 as a colorless oil (2.26 g, 80%).

$^1H$ NMR (400 MHz, $CDCl_3$) $\delta_H$ 6.05 (m, 1H), 5.95 (m, 1H), 4.72 (dt, J=7.2, 1.8 Hz, 1H), 3.71 (m, 1H), 3.55 (m, 1H), 3.07 (d, J=3.2, —OH), 2.49-2.41 (dddd, J=12.0, 9.6, 4.8, 2.9 Hz, 1H), 2.29-2.21 (ddd, J=14.5, 13.0, 13.0 Hz, 1H), 2.20-2.12 (dddd, J=11.4, 9.4, 4.4, 2.8 Hz, 1H), 2.01-1.92 (m, 1H), 1.84-1.73 (ddd, J=14.4, 12.9, 12.9 Hz, 1H), 0.89 (s, 9H), 0.02 (s, 3H), 0.00 (s, 3H).

General Procedure for the Preparation of Compounds 3b-3e

A solution of compound 2 (1 mmol) in 6 ml of dry THF was added dropwise to a suspended solution of KH (1.1 mmol) in 20 ml of dry THF at 0° C. The mixture was stirred at 0° C. for 30 min. The alkylating reagents (2.2 mmol) were added dropwise at 0° C. After completion of addition, the reaction mixture was warmed to room temperature and kept stirring for another 3 h. The reaction was quenched with saturated $NH_4Cl$ solution. The organic solution was dried over $MgSO_4$ and concentrated in vacuo. The residue was purified by flash chromatography on silica gel (hexanes/EtOAc 9:1) to give the desired compound.

Synthesis of Compound 3b

Compound 2 (500 mg, 2.07 mmol) was treated with KH (90 mg, 2.272 mmol) and bromoethane (450 mg, 4.132 mmol), according to the general method described above, to give pure product 3b (colourless oil, 400 mg, 72%). $^1$H NMR($CDCl_3$, 400 MHz) $\delta_H$ 6.04 (m, 1H), 5.94 (m, 1H), 4.25 (dt, J=7.2, 1.8 Hz, 1H), 3.71 (m, 2H), 3.44 (m, 1H), 3.32 (m, 1H), 2.49-2.41 (dddd, J=12.0, 9.6, 4.8, 2.9 Hz, 1H), 2.29-2.21 (ddd, J=14.5, 13.0, 13.0 Hz, 1H), 2.20-2.12 (dddd, J=11.4, 9.4, 4.4, 2.8 Hz, 1H), 2.01-1.92 (m, 1H), 1.84-1.73 (ddd, J=14.4, 12.9, 12.9 Hz, 1H), 1.17 (t, J=7.2 Hz, 3H), 0.89 (s, 9H), 0.02 (s, 6H).

Synthesis of Compound 3c

Compound 2 (500 mg, 2.07 mmol) was treated with KH (90 mg, 2.27 mmol) and 1-bromopropane (507 mg, 4.128 mmol), according to the general method described above, to give pure product 3c (colourless oil, 400 mg, 68%). $^1$H NMR ($CDCl_3$, 400 MHz) $\delta_H$ 6.01 (m, 1H), 5.95 (m, 1H), 4.23 (dt, J=7.2, 1.8 Hz, 1H), 3.69 (m, 2H), 3.44 (m, 1H), 3.32 (m, 1H), 2.49-2.41 (dddd, J=12.0, 9.6, 4.8, 2.9 Hz, 1H), 2.29-2.21 (ddd, J=14.5, 13.0, 13.0 Hz, 1H), 2.20-2.12 (dddd, J=11.4, 9.4, 4.4, 2.8 Hz, 1H), 2.01-1.92 (m, 1H), 1.84-1.73 (ddd, J=14.4, 12.9, 12.9 Hz, 1H), 1.53-1.63 (m, 2H), 0.91 (t, J=7.2 Hz, 3H), 0.90 (s, 9H), 0.02 (s, 6H).

Synthesis of Compound 3d

Compound 2 (500 mg, 2.07 mmol) was treated with KH (90 mg, 2.27 mmol) and 1-bromobutane (566 mg, 4.132 mmol), according to the general method described above, to give pure product 3d (colourless oil, 425 mg, 69%). $^1$H NMR($CDCl_3$, 400 MHz) $\delta_H$ 6.01 (m, 1H), 5.95 (m, 1H), 4.22 (dt, J=7.2, 1.8 Hz, 1H), 3.68 (m, 2H), 3.44 (m, 1H), 3.32 (m, 1H), 2.43-2.35 (dddd, J=12.0, 9.6, 4.8, 2.9 Hz, 1H), 2.34-2.25 (ddd, J=14.5, 13.0, 13.0 Hz, 1H), 2.20-2.13 (dddd, J=11.4, 9.4, 4.4, 2.8 Hz, 1H), 2.01-1.92 (m, 1H), 1.73-1.64 (ddd, J=14.4, 12.9, 12.9 Hz, 1H), 1.61-1.51 (m, 2H), 1.43-1.33 (m, 2H), 0.91 (t, J=7.2 Hz, 3H), 0.90 (s, 9H), 0.01 (s, 6H).

Synthesis of Compound 3e

Compound 2 (500 mg, 2.07 mmol) was treated with KH (90 mg, 2.27 mmol) and 1-iodopentane (818 mg, 4.132 mmol), according to the general method described in above section, to give pure product 3e (colourless oil, 439 mg, 68%). $^1$H NMR($CDCl_3$, 400 MHz) $\delta_H$ 6.01 (m, 1H), 5.95 (m, 1H), 4.22 (dt, J=7.2, 1.8 Hz, 1H), 3.69 (m, 2H), 3.45 (m, 1H), 3.32 (m, 1H), 2.43-2.35 (dddd, J=12.0, 9.6, 4.8, 2.9 Hz, 1H), 2.34-2.25 (ddd, J=14.5, 13.0, 13.0 Hz, 1H), 2.20-2.13 (dddd, J=11.4, 9.4, 4.4, 2.8 Hz, 1H), 2.01-1.92 (m, 1H), 1.73-1.64 (ddd, J=14.4, 12.9, 12.9 Hz, 1H), 1.60-1.52 (m, 2H) 1.37-1.28 (m, 4H), 0.91 (t, J=7.2 Hz, 3H), 0.90 (s, 9H), 0.01 (s, 6H).

General Procedure for Synthesis of Compounds 4b-4e

To a stirred solution of compounds 3b-3e (1 mmol) in 10 ml of THF was added tert-butyl ammonium fluoride (TBAF) (2 mmol) at room temperature. After 12 h, the reaction mixture was diluted with EtOAc, the organic layer was separated and washed with saturated $NH_4Cl$ and brine solutions. The organic layer was dried over $MgSO_4$ and concentrated in vacuo. The crude product was purified by flash column chromatography on silica gel (hexanes/EtOAc 7:3) to afford the desired product.

General Procedure for the Racemic cy{$R_3$, 1} Compounds

A solution of compounds 4b-4e (1 mmol) in 6 ml of dry THF was added dropwise to a suspended solution of KH (1.1 mmol) in 20 ml of dry THF at 0° C. The mixture was stirred at 0° C. for 30 mins. The alkylating reagents (2.2 mmol) were added dropwise at 0° C. After completion of addition, the reaction mixture was warmed to room temperature and kept stirring for another 3 h. The reaction was quenched with saturated $NH_4Cl$ solution. The organic solution was dried over $MgSO_4$ and concentrated in vacuo. The residue was purified by flash chromatography on silica gel (hexanes/EtOAc 9:1) to give the desired compound.

Synthesis of cy{1,1}

Compound 1 (100 mg, 0.78 mmol) was treated with KH (34 mg, 0.859 mmol) and iodomethane (424 mg, 3.124 mmol), according to the general method described in the section above, to give pure product cy{1,1} (colourless oil, 30 mg, 25%). $^1$H NMR($CDCl_3$, 400 MHz) $\delta_H$6.01 (m, 1H), 5.95 (m, 1H), 4.14 (dt, J=7.2, 1.8 Hz, 1H), 3.48 (td, J=6.4, 2.1 Hz, 1H), 3.37 (s, 3H), 3.34 (s, 3H), 2.43-2.35 (dddd, J=12.0, 9.6, 4.8, 2.9 Hz, 1H), 2.34-2.25 (ddd, J=14.5, 13.0, 13.0 Hz, 1H), 2.20-2.13 (dddd, J=11.4, 9.4, 4.4, 2.8 Hz, 1H), 2.01-1.99 (m, 1H), 1.73-1.64 (ddd, J=14.4, 12.9, 12.9 Hz, 1H); MS m/z (relative intensity): 157 (M+1,10%), 149 (25%), 109 (50%), 69 (100%).

Synthesis of cy{2, 1}

Compound 4b (250 mg, 1.6 mmol) was treated with KH (76 mg, 19.2 mmol) and iodomethane (454 mg, 3.2 mmol), according to the general method described above, to give pure product cy{2, 1} (colourless oil, 220 mg, 81%). $^1$H NMR ($CDCl_3$, 400 MHz) $\delta_H$ 6.01 (m, 1H), 5.94 (m, 1H), 4.25 (dt, J=7.2, 1.8 Hz, 1H), 3.60-3.52 (m, 1H), 3.52-3.43 (m, 3H), 3.37 (s, 3H), 2.43-2.35 (dddd, J=12.0, 9.6, 4.8, 2.9 Hz, 1H), 2.34-2.25 (ddd, J=14.5, 13.0, 13.0 Hz, 1H), 2.20-2.13 (dddd, J=11.4, 9.4, 4.4, 2.8 Hz, 1H), 2.01-1.92 (m, 1H), 1.73-1.64 (ddd, J=14.4, 12.9, 12.9 Hz, 1H), 1.20 (t, J=7.2 Hz, 3H); MS m/z (relative intensity): 171 (M+1, 1%), 169 (M−1, 25%), 125(100%).

Synthesis of cy{3, 1}

Compound 4c (440 mg, 2.58 mmol) was treated with KH (120 mg, 3 mmol) and iodomethane (734 mg, 5.176 mmol), according to the general method described above, to give pure product cy{3, 1} (colourless oil, 300 mg, 63%). $^1$H NMR ($CDCl_3$, 400 MHz) $\delta_H$ 6.01 (m, 1H), 5.95 (m, 1H), 4.23 (dt, J=7.2, 1.8 Hz, 1H), 3.55-3.42 (m, 3H), 3.41-3.33 (m, 1H), 3.38 (s, 3H), 2.43-2.35 (dddd, J=12.0, 9.6, 4.8, 2.9 Hz, 1H), 2.34-2.25 (ddd, J=14.5, 13.0, 13.0 Hz, 1H), 2.20-2.13 (dddd, J=11.4, 9.4, 4.4, 2.8 Hz, 1H), 2.01-1.92 (m, 1H), 1.73-1.64 (ddd, J=14.4, 12.9, 12.9 Hz, 1H), 1.63-1.54 (m, 2H), 0.91 (t, J=7.2 Hz, 3H); MS m/z (relative intensity): 185 (M+1, 1%), 125 (75%), 93(100%).

Synthesis of cy{4, 1}

Compound 4d (500 mg, 2.71 mmol) was treated with KH (130 mg, 3.26 mmol) and iodomethane (771 mg, 5.43 mmol), according to the general method described above, to give pure product cy{4, 1} (colourless oil, 438 mg, 82%). $^1$H NMR($CDCl_3$, 400 MHz) $\delta_H$ 6.01 (m, 1H), 5.95 (m, 1H), 4.22 (dt, J=7.2, 1.8 Hz, 1H), 3.54-3.44 (m, 3H), 3.41 (m, 1H), 3.38 (s, 3H), 2.43-2.35 (dddd, J=12.0, 9.6, 4.8, 2.9 Hz, 1H), 2.34-2.25 (ddd, J=14.5, 13.0, 13.0 Hz, 1H), 2.20-2.13 (dddd, J=11.4, 9.4, 4.4, 2.8 Hz, 1H), 2.01-1.92 (m, 1H), 1.73-1.64 (ddd, J=14.4, 12.9, 12.9 Hz, 1H), 1.61-1.51 (m, 2H), 1.43-1.33 (m, 2H), 0.91 (t, J=7.2 Hz, 3H); MS m/z (relative intensity): 197 (M−1, 2.5%), 125 (25%), 109 (75%), 93 (100%).

Synthesis of cy{5, 1}

Compound 4e (280 mg, 1.414 mmol) was treated with KH (67 mg, 1.696 mmol) and iodomethane (401 mg, 2.228 mmol), according to the general method described above, to give pure product cy{5,1} (colourless oil, 220 mg, 74%). $^1$H NMR($CDCl_3$, 400 MHz) $\delta_H$ 6.01 (m, 1H), 5.95 (m, 1H), 4.22 (dt, J=7.2, 1.8 Hz, 1H), 3.53-3.44 (m, 3H), 3.43-3.36 (m, 1H), 3.38 (s, 3H), 2.43-2.35 (dddd J=12.0, 9.6, 4.8, 2.9 Hz, 1H), 2.34-2.25 (ddd, J=14.5, 13.0, 13.0 Hz, 1H), 2.20-2.13 (dddd, J=11.4, 9.4, 4.4, 2.8 Hz, 1H), 2.01-1.92 (m, 1H), 1.73-1.64 (ddd, J=14.4, 12.9, 12.9 Hz, 1H), 1.60-1.52 (m, 2H) 1.37-1.28 (m, 4H), 0.91 (t, J=7.2 Hz, 3H); MS m/z (relative intensity): 211 (M−1, 2.5%), 159 (50%), 91(100%).

Electrophysiology Bioassay

Electrophysiological (EP) recordings were carried out on the olfactory sensory organ on the *Varroa* foreleg. The foreleg was dissected at the base and mounted between two glass capillaries filled with KCl solution (0.1 N), each containing a silver recording electrode thus closing the electrical circuit. A constant flow of charcoal-filtered and humidified air was blown towards the organ at a rate of 100 ml/min using a stimulus flow controller (model CS-05; Syntech, Hilversum, the Netherlands).

The effect of the disruptive compounds on the EP response was measured relative to the response to a positive stimulus (honey bee headspace). The headspace was presented by puffing charcoal-filtered air (1000 ml/min, for 1 second) through a glass jar that contained freshly freeze-killed nurse bees (1, 5 or 10 bees were tested) kept in a controlled environment (32-34 C.°, 62-70%). Head space of an empty jar kept under the same conditions was used as control (FIG. 2A). The same foreleg was used to test all the treatments.

FIG. 2A shows the experimental setup for evaluating electrophysiology (EP) with an isolated *Varroa* foreleg, stimulated with the headspace volatiles of freshly caught honey bees in a jar. FIG. 2B shows the typical traces of *Varroa* foreleg responses to air (left) and honey bee volatiles (right). FIG. 2C shows the electrophysiological response amplitude of the *Varroa* foreleg. FIG. 2D shows a comparison between the responses to the headspaces of different numbers of bees: 1, 5 and 10 bees and no bee (empty jar), as analyzed using repeated ANOVA measures followed by Tukey-Kramer post hoc tests. The bars marked by different letters are significantly different, $p<0.05$ (n=6).

To prepare EP cartridges of the potential disrupting compounds, 1 μl of the compound dissolved in hexane was pipetted onto a piece of filter paper (Whatman No 1) which is placed in a glass Pasteur pipette and exposed to air for 30 s to allow solvent to evaporate. Three different stimuli were tested: a "positive stimulus" (five bees' headspace), a "positive stimulus+compound", a control stimulus "Air" (an empty jar) and hexane.

Figure 3A:
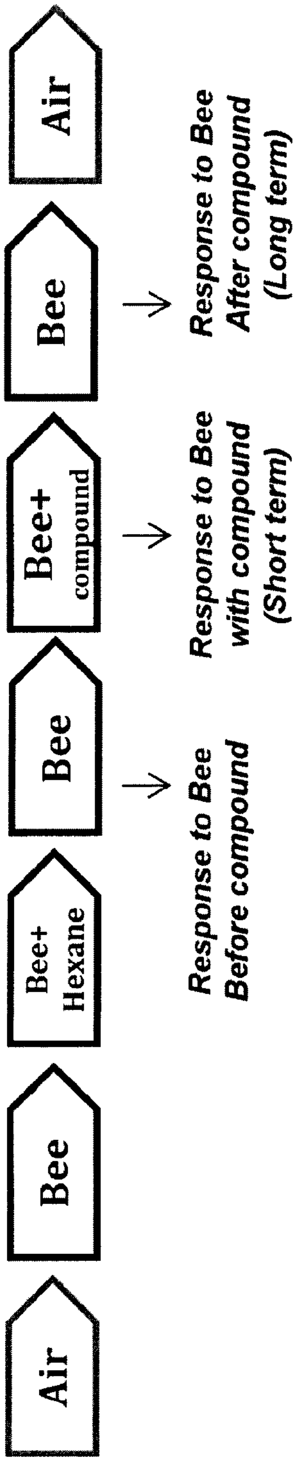
FIG. 3A is a schematic diagram showing the order of chemicals used to evaluate the *Varroa* foreleg stimulations and terminology used for the corresponding responses. The time interval between each chemical stimulus was 30 s, unless otherwise stated. The chemical stimuli were: air, headspace of five nurse bees (bee stimulus), bee stimulus together with a test compound (bee stimulus+comp) or of the hexane control (bee stimulus+hexane). In italics, below the stimuli, are the names of the values presented in the results.

In all experiments, the stimuli were given in the same order on the same forelegs as presented in FIG. 3A. When more than one compound was tested, the compounds were applied in a random order. At least six different *Varroa* forelegs were tested (one from each individual) for each experiment.

The EP response (mV) was amplified and recorded by a PC via an IDAC-232 for data acquisition using the "EAG 2000" and "GCEAD-2000" softwares (all Syntech). For the organ to recover and to prevent adaptation, intervals of 30 sec was allowed between each stimulus unless specified otherwise.

The response amplitude was normalized relative to the response of the same organ to the control stimulus (Eq. 1). Only individuals that showed a higher response to the "positive stimulus" than to the control stimulus prior to the exposure to the compounds were used for statistical analysis. The effect of the compounds was evaluated relative to the response to the "positive stimulus" before the exposure to the tested compound. Two kinds of effect were evaluated: the effect that occurred in the presence of the compound termed "short term effect", and the effect following the administration of the compound but not in its presence termed "long term effect".

$$N = \frac{(\text{response to stimulus} - \text{response to air (control)})}{\text{response to stimulus}} \cdot 100 + 100 \quad \text{(Eq. 1)}$$

Normalization Equation 1.

Res—Response amplitude to a stimulus (mV), Air—Response amplitude to air (mV), N— Response amplitude normalized relative to the response to air (%).

Behavioral Bioassays

The effect of the compounds on the *Varroa*'s host preference was tested in a two-choice bioassay. In this bioassay, a single mite was placed in the center of the arena (90 mm diameter and 17 mm deep glass Petri dish) and was presented with a choice of a freshly killed forager or a nurse, respectively placed on the opposite sides of the arena. The experiments were conducted in a controlled dark environment, at 34-35° C. and 60-70% relative humidity (RH, simulating conditions in a bee hive). The *Varroa* choice was examined in the presence of 0.01 μg, 0.1 μg, and 10 μg of the compound dissolved in 1 μl hexane or in the presence of 1 μl pure hexane, as control. The compound or hexane, were placed right above the *Varroa* on the inner side of the cover plate, on a piece of parafilm for slow release (5*5 mm, Bemis, USA). Each dose was tested at least in 3 replicated experiments; in each experiment 10 to 19 mites were tested for each treatment (Compound or hexane). The mite position on a nurse, a forager or elsewhere was documented after 120 minutes. *Varroa*'s host preference between a forager and a nurse bee was calculated as the percentage of total mites reaching any of the hosts. *Varroa*'s ability to reach any of the hosts was calculated as the percentage of viable mites by the end of the experiment out of total tested mites.

Statistical Analysis

For the electrophysiology assays, the original data in mV, or the normalized data in percentages were analyzed using ANOVA Repeated Measures, followed by a post hoc Tukey-Kramer test. A Bonferroni correction was used when needed.

For behavioral assays, logistic regression analysis was used to assess the dose effect of the compounds on *Varroa* host preference. Odds ratio and 95% confidence intervals are reported. A possible effect of the compounds on *Varroa* ability to reach any of the hosts was assessed using Chi-square test on proportion of mites reaching any of the hosts, out of the viable mites. All Statistical procedures were carried out with the SAS JMP® Start statistic program 7.0.2.

Molecular Modeling

Structures were drawn in ChemDraw and imported into ChemBio3D Ultra v. 11 (CambridgeSoft, Cambridge, Mass., USA). Each model was first minimized with MM2 molecular mechanics model, and then with PM3 model, a semiempirical method. In both minimizations all atoms were allowed to move freely, and PM3 minimizations were done with the closed shell wave function, the EF optimizer, until the RMS gradient was ≤0.1. Initial minimization was done in a vacuum, followed by minimization in water and in chloroform. No significant differences were seen between the three environments, so the structures obtained in chloroform (which mimics the hydrophobic environment of potential binding sites on or in proteins) were used for further exploration. To establish the breadth of the minima, double dihedral angle plots were constructed for all sets of neighboring C and/or O atoms around which free rotation is possible. Between dihedral angle explorations, the model was "heated" by short molecular dynamics trajectory (1000 iterations) at 700 K, after which the last structure was minimized again in PM3. For overlaying of structures, the global energy minima of the two structures were used, with the software's overlay algorithm. Overlays were done with cy{4,1} as the target structure or with 3b{2,2} as the target. Both overlay simulations delineated a similar space.

Results

Electrophysiology

To test the disruption of the *Varroa* host detection nurses' headspace was selected as a positive stimulus. Stimulation of the *Varroa* foreleg with headspace from different number of bees (1, 5 or 10) indicated that although one honey bee head space elicited some response in the *Varroa* leg, only stimuli of 5 and 10 bees evoked significantly higher response than air ($F(3, 15)=4.75$, $p=0.016$, ANOVA repeated measures followed be a Bonferroni correction; FIG. 2C). As 10 bees' headspace did not add a significant increase in the response amplitude the headspace of five bees was used in further experiments.

Figure 3B:
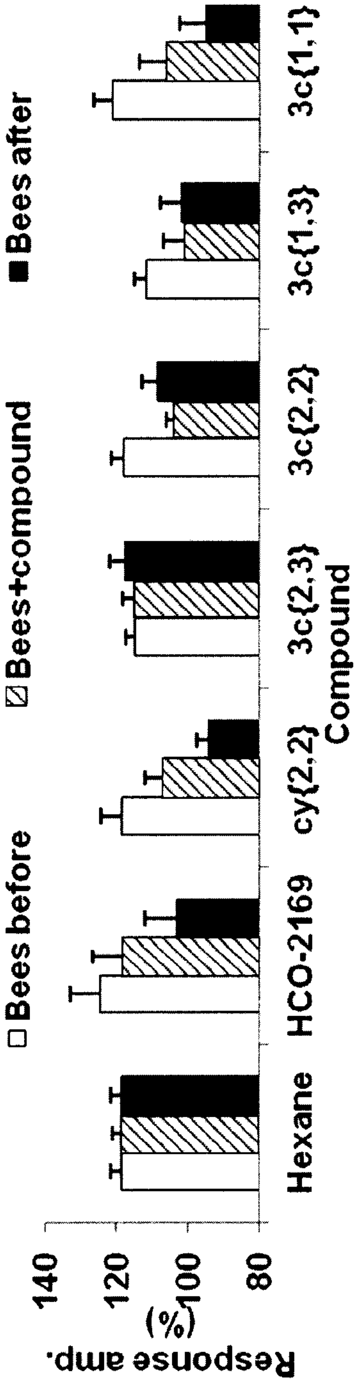
FIG. 3B is a bar graph showing an initial screen of the *Varroa* foreleg electrophysiological response to different stimuli, all loaded at 10 μg in the stimulus cartridge (normalized values against the response to air %, average+SE). For the bee stimuli, the headspace from 5 nurse bees was used. Bars marked by different letters are significantly different, ANOVA repeated measures, $p<0.05$, $n=10$.
Figure 3C:
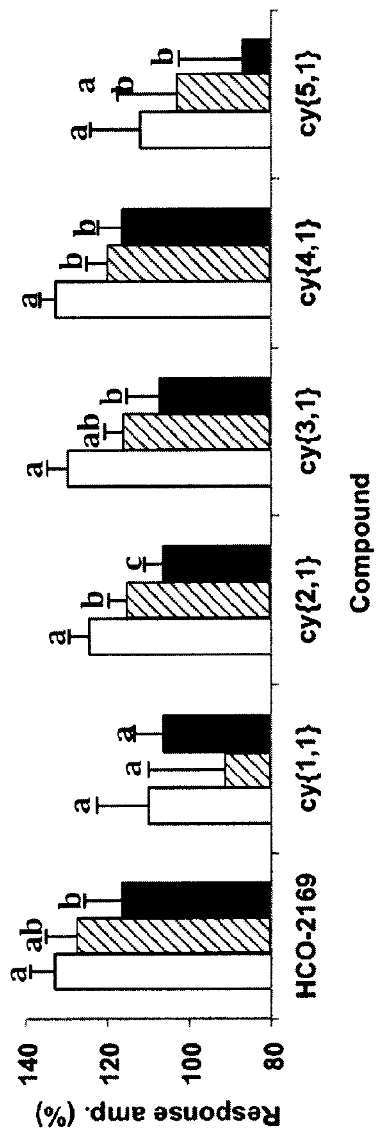
FIG. 3C is a bar graph showing the results from evaluation of the individual components of an example of a blend HCO-2169 (cy{1,1}, cy{2,1}, cy{3,1}, cy{4,1} and cy{5, 1}) at 10 μg doses (n=10).
Figure 3D:
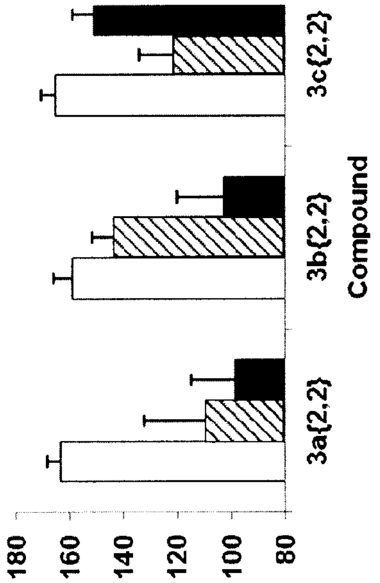
FIG. 3D is a bar graph showing the results from evaluation of three isomers of diethyloxybenzene at 10 μg doses (n=6).

FIG. 3A-3D shows the results from electrophysiological screening of the compounds. FIG. 3A shows the order of the *Varroa* foreleg stimulations and terminology used for the corresponding responses. The time interval between each stimulus was 30 s, unless otherwise stated. The stimuli were: air, headspace of five nurse bees ("Bee stimulus"), bee stimulus together with the compound ("Bee stimulus+comp") or of the hexane control ("Bee stimulus+hexane"). In italics, below the stimuli, are the names of the values presented in the results. FIG. 3B shows the results from an initial screen of the *Varroa* foreleg electrophysiological response to different stimuli, all loaded at 10 mg in the stimulus cartridge. For the bee stimuli, the headspace from 5 nurse bees was used. (normalized values against the response to air %, average+SE) (n=10). FIG. 3C shows the testing of the individual components of the blend HCO-2169 at 10 mg doses (n=10). FIG. 3D shows the results from an experiment with the three isomers of diethyoxybenzene at 10 μg doses. ANOVA repeated measures were followed by Tukey-Kramer post hoc tests. Bars marked by different letters are significantly different, $p<0.05$, (n=5-6).

FIGS. 4A-4C show dose responses of long-term inhibitory compounds cy{4,1}, 3b{2,2} and cy{2,2}, respectively. The responses of the *Varroa* forelegs to stimulation with different amounts of each compound and with the headspace from 5 nurse bees (normalized values against the response to air %, average+SE). ANOVA repeated measures were followed by Tukey-Kramer post hoc tests. Bars marked by different letters are significantly different, $p<0.05$, (n=6-7).

Figure 5A:
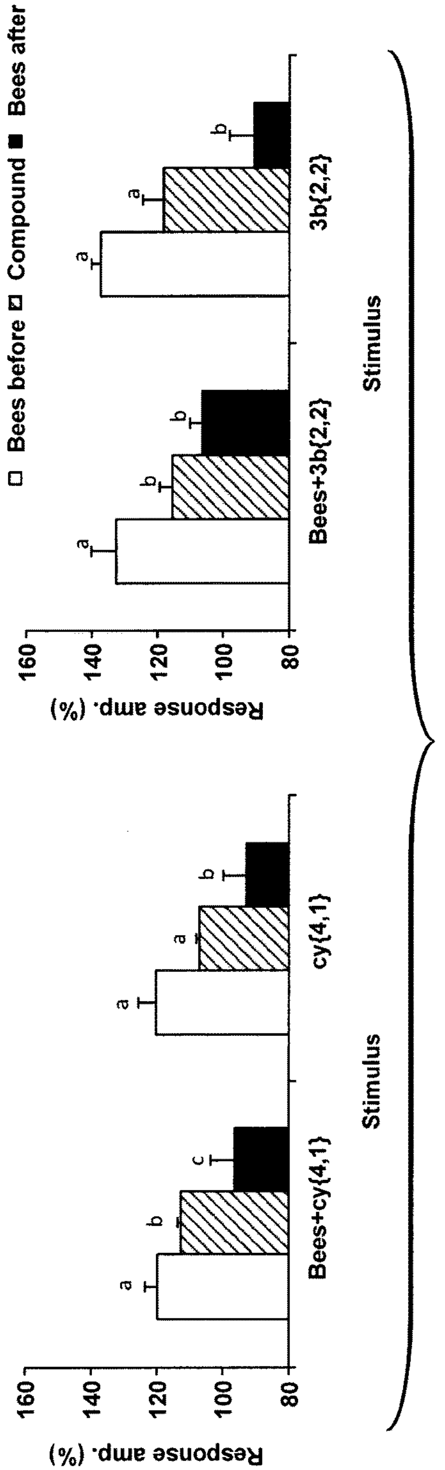
FIGS. 5A-5B are bar graphs showing the results of detailed evaluation of the long-term inhibitory effect of embodiments of active compounds.
Figure 5B:
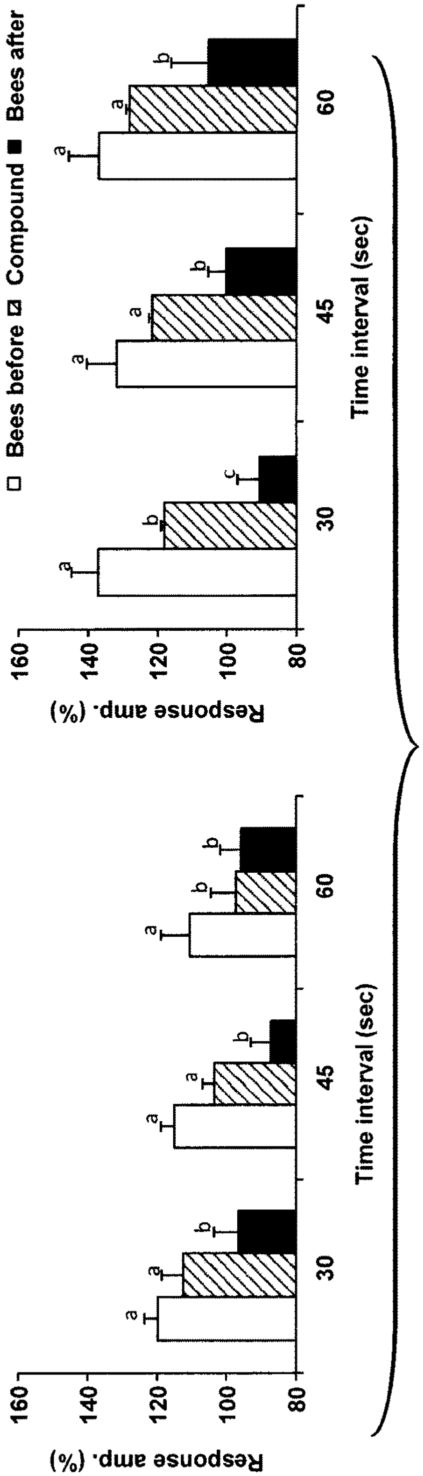

FIGS. 5A-5B show a detailed evaluation of the long-term inhibitory effect of the most active compounds. FIG. 5A shows the effect of 0.1 μg cy{4,1} (left) and 3b{2,2} (right), with and without a simultaneous stimulus of the headspace volatiles from 5 nurse bees, on the electrophysiological response of the *Varroa* foreleg. The data are normalized values (%, average+SE): bars marked by different letters are significantly different, ANOVA repeated measures, $p<0.05$, n=6. FIG. 5B shows the longevity of the inhibitory effect of 0.1 μg cy{4,1} (left) or 0.1 mg 3b {2,2} (right) on *Varroa* foreleg electrophysiological responses. The time interval between the compound stimulus and the pure bee stimulus was varied. (normalized values against the response to air %, average+SE). ANOVA repeated measures followed by Tukey-Kramer post hoc tests. Bars marked by different letters are significantly different, $p<0.05$, (n=6).

Figure 6B:
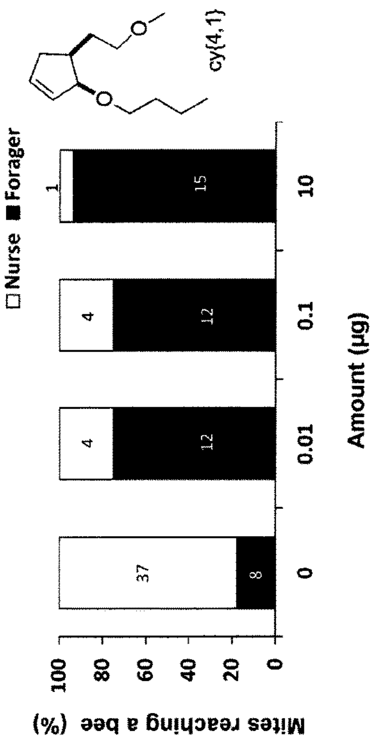
Figure 6C:
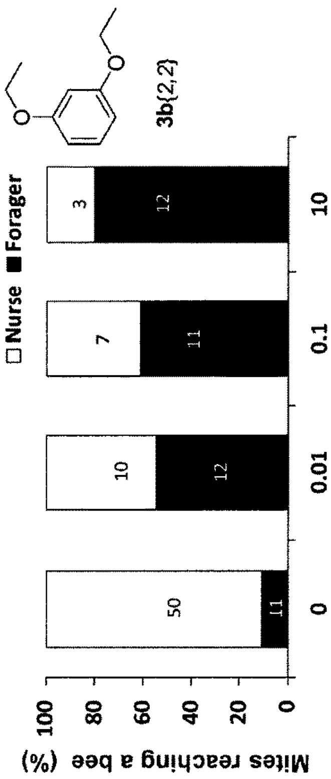
Figure 6D:
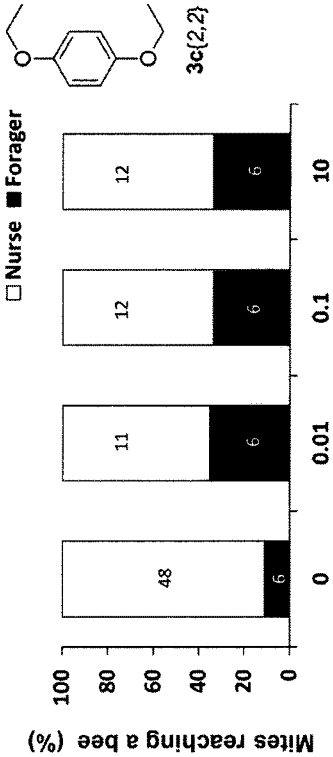

FIGS. 6A-6D show the effect of selected compounds on *Varroa* host choice between a nurse and a forager bee. FIG. 6A depicts the experimental setup. The test compound did not contact the mite, and the mite could move around and choose between a freshly killed nurse or forager. FIG. 6B shows the effect of cy{4,1} at different doses (0.01 μg, 0.1 μg, 10 μg) ($p<0.0001$, OR=82.8, (95% CI 0.49-1.02): data are the percentage of *Varroa* that selected a particular host 180 min from the beginning of the experiment in the presence of hexane (control) or disrupting compound. Numbers within the bars show the number of *Varroa* choosing each of the hosts. FIG. 6C shows the effect of 3b{2,2} ($p<0.0001$. OR=35.1, (95% CI 0.4-0.82). FIG. 6D shows the effect of 3c{2,2} ($p<0.0048$, OR=5.41 (95% CI 0.09-0.48). Logistic regression, $p<0.001$.

*Varroa* Responses to Sequential Stimuli of Bee Headspace

In order to check for a possible habituation of the *Varroa* foreleg to honey bee volatiles, and the response stability over time, sequential stimuli of five-bee headspace were puffed at intervals of 30 seconds. Comparing the response amplitudes in 7 different *Varroa* mites, no significant difference was found between the response amplitudes ($F(2, 12)=0.0407$, $p=0.96$, ANOVA repeated measures), and the response remained stable for at least 20 min.

Figure 7:
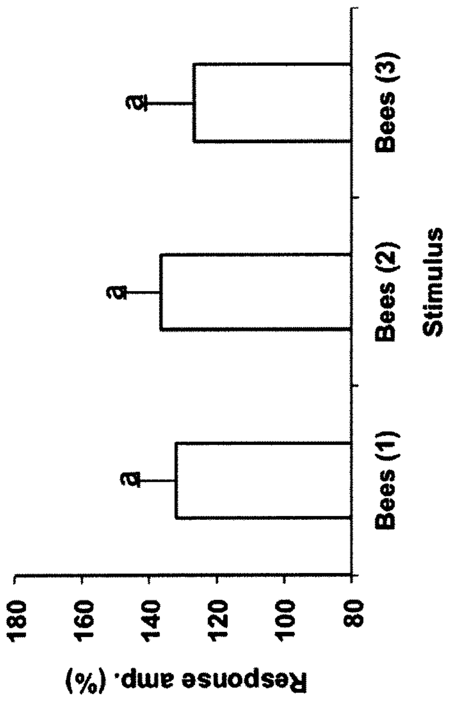
FIG. 7 is a bar graph showing *Varroa* foreleg electrophysiological response amplitude, specifically a comparison between the responses to three sequential stimuli of five-bee headspace. ANOVA repeated measures followed by Tukey-Kramer post hoc tests. Bars marked by different letters are significantly different, $F(2, 12)=0.0407$, $p=0.96$ (n=7).

FIG. 7 shows a comparison of the *Varroa* foreleg electrophysiological responses to three sequential stimuli of five-bee headspace. ANOVA repeated measures were followed by Tukey-Kramer post hoc tests. Bars marked by different letters are significantly different, F(2,12)=0.0407, p=0.96 (n=7).

The Effect of Compounds on the *Varroa* Response to Bees' Headspace

The disruptive effect of 6 different compounds on the electrophysiological response of *Varroa* foreleg to honey bee headspace was tested, by sequentially stimulating the foreleg with air, bee headspace or mixed bee headspace+compound stimuli (FIG. 3A).

A significant inhibitory effect on the sensory organ was apparent for most of the tested compounds except for the hexane-control and 3c{2,3} at 10 μg (ANOVA repeated measures, p<0.05). The impact of the inhibiting compounds on mite responses to honeybee headspace was not the same. A significant short-term inhibitory effect was found for compounds 3c{2,2} and cy{2,2} (F(2, 16)=8.92, p=0.002; F(2, 16)=42.8, p<0.0001), while a significant long-term effect was observed with 3c{1,1}, cy{2,2} and the blend, HCO-2169 (F(2, 16)=3.89, p=0.04; F(2, 16)=19, p<0.0001) (FIG. 3B). This long-term inhibition appeared stronger than the short-term effect for cy{2,2} and HCO-2169, but it was eliminated in a fourth stimulation with bee headspace that was applied after stimulation with air (data not shown). In the present study, there were different structure-activity relationships for the short-term and long-term effects. For example, 3c{1,1}, 3c{2,2} and cy{2,2} were similar in their short-term effect, whereas 3c{2,3} was not active. In terms of the long-term effect the activity was: cy{2,2}>3c{1, 1}≅3c{2,2}; HCO-2169 and 3c{2,3} were not active.

HCO2169 is a blend of methyl-substituted cy compounds: cy{1-5,1}. To reveal structure-activity relationship of the inhibitory effect, components of HCO-2169: cy{1,1}, cy{2, 1}, cy{3,1}, cy{4,1} and cy{5,1} were studied. The different components as well as the whole mixture (HCO-2169, as a positive control) were tested in a random order. Except for cy{1,1}, all of the tested compounds had a long-term inhibiting effect on the *Varroa* response to bee headspace (FIG. 3C). The three most effective compounds in that series were: cy{4,1}, cy{3,1} and cy{2,1} (F(2, 18)=10.7, p=0.0009; F(2, 18)=4.1, p=0.03; F(2, 18)=14.6, p=0.0002). To follow up on the structure-activity relationship of the dialkoxybenzenes, experiments with the three isomers of diethoxybenzene, 3a{2,2}, 3b{2,2} and 3c{2,2}, as well as cy{2,2} and 3c{1,1} were performed. The isomers of diethoxybenzene differed in their activity: 3c{2,2} was the best short-term inhibitor but showed no long-term inhibition, whereas 3b{2,2} was opposite and 3a{2,2} exhibited a long term inhibition (F(2, 10)=9.9, p=0.004; F(2, 10)=16.8, p=0.001; F(2, 10)=5.9, p=0.026) (FIG. 3D). Compound cy{2,2} showed moderate long-term inhibition (see below). For 3c{1,1} the long-term inhibition at the higher doses of 1 or 10 μg was confirmed (FIG. 8B).

Figure 8A:
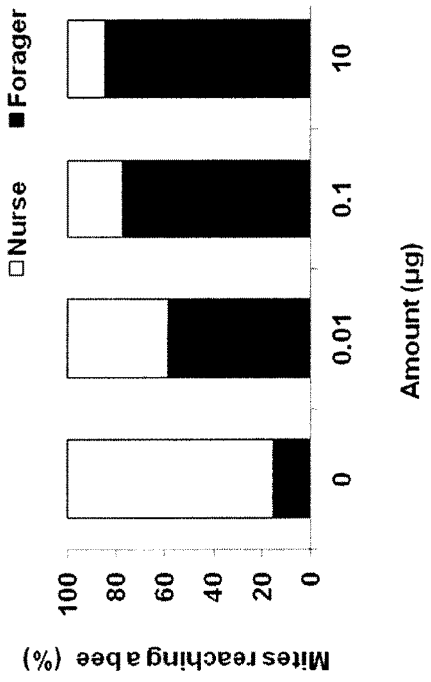
FIG. 8A is a bar graph showing the effect of an embodiment of the compounds of the present disclosure (cy{2,2}) on *Varroa* host choice between a nurse and a forager bee. The compound was tested at different doses (0.01 μg, 0.1 μg, 10 μg) (OR=54, (95% CI 15.3-231.9): data are the percentage of *Varroa* that selected a particular host 180 min from the beginning of the experiment in the presence of hexane (control) or disrupting compound. Numbers within the bars show the number of *Varroa* choosing each of the hosts.
Figure 8B:
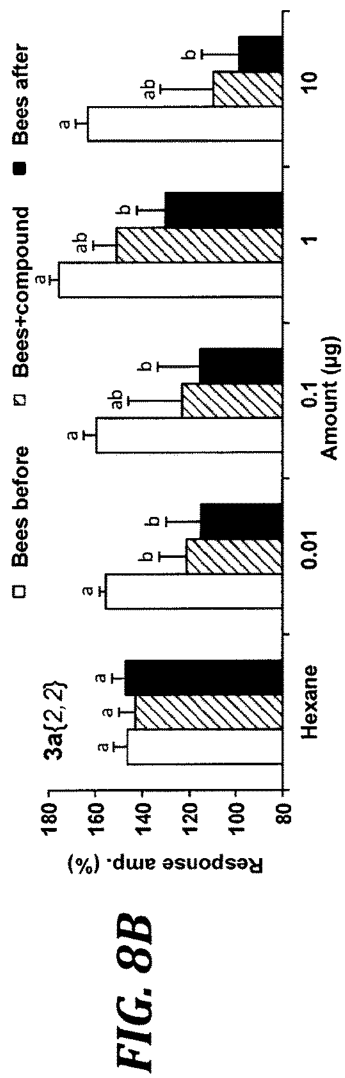
FIGS. 8B-8D are bar graphs showing the dose responses of examples of long-term inhibitory compounds 3a{2,2}, 3c{2,2} and 3c{1,1}, respectively. The responses of the *Varroa* forelegs to stimulation with different amounts of each compound and with the headspace from 5 nurse bees (normalized values against the response to air %, average+SE) are shown. ANOVA repeated measures were followed by Tukey-Kramer post hoc tests. Bars marked by different letters are significantly different, $p<0.05$, (n=6).
Figure 8C:
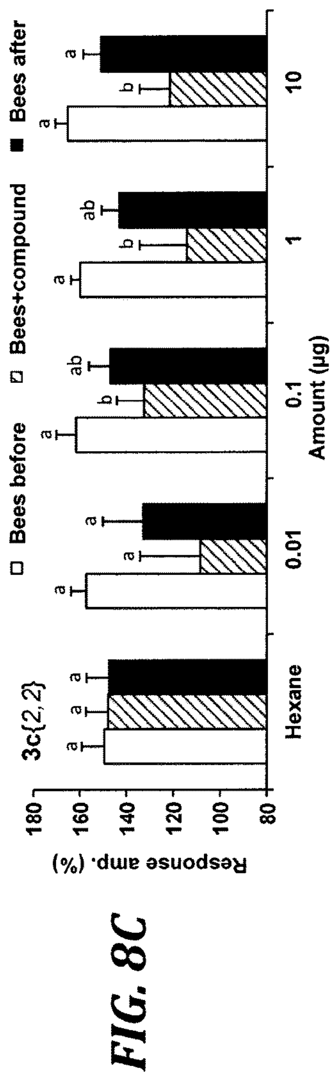
Figure 8D:
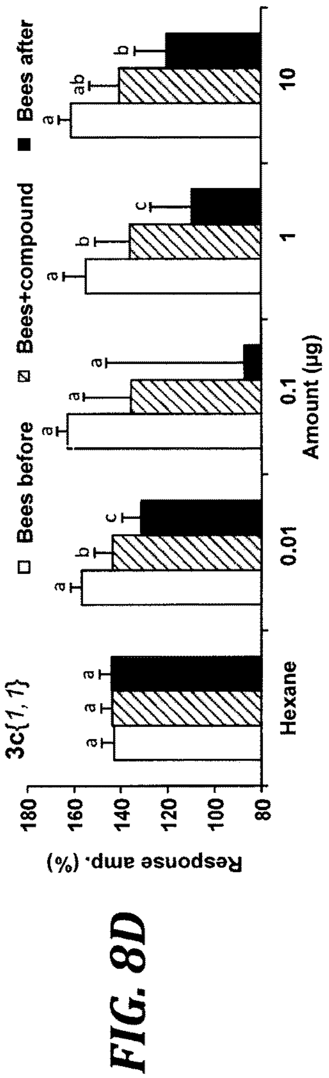

FIG. 8A shows the effect of cy{2,2} on *Varroa* host choice between a nurse and a forager bee. The compound was tested at different doses (0.01 μs, 0.1 μg, 10 μg) (OR=54, (95% CI 15.3-231.9): data are the percentage of *Varroa* that selected a particular host 180 min from the beginning of the experiment in the presence of hexane (control) or disrupting compound. Numbers within the bars show the number of *Varroa* choosing each of the hosts. FIG. 8B shows the dose responses of long-term inhibitory compounds 3a{2,2}, 3c{2, 2} and 3c{1,1}. The responses of the *Varroa* forelegs to stimulation with different amounts of each compound and with the headspace from 5 nurse bees (normalized values against the response to air %, average+SE). ANOVA repeated measures followed by Tukey-Kramer post hoc tests. Bars marked by different letters are significantly different, p<0.05, (n=6).

The specificity of the *Varroa* leg response to cy{4,1} was further evaluated, because it is less volatile than cy{2,1}, cy{3,1} or 3b{2,2} and therefore easier to work with. First, a dose response was measured. The dose of 0.01 μg was inactive both short and long-term (F(2, 12)=2.9, p=0.08). Doses of 0.1 μg and higher were all active long-term, and short-term only for 1 μg dose (F(2, 12)=14.9, p=0.0005) (FIGURE. 4). The optimal dose appears to be 0.1 μg. This dose was used in subsequent experiments with cy{4,1}. Similarly, dose responses were obtained for the other two long-term inhibitors, cy{2,2} and 3b{2,2}. For 3b{2,2} a long-term inhibition was found for all of the doses (0.01 μg F(2, 10)=20.4, p=0.0001; 0.1 μs F(2, 10)=15.4, p=0.001; 1 μg F(2, 10)=23.4, p=0.0001; 10 μg F(2, 10)=16.8, p=0.001), while a short-term inhibition was observed only for dose 0.1 μg. On the other hand, cy{2,2} was only long-term active in doses 0.1 and 1 μg (F(2, 10)=13, p=0.002; F(2, 10)=9.7, p=0.005). When 0.1 μg of cy{4,1} stimulus was given alone, the compound elicited a response that was greater than the response to air and not significantly different from the honeybee head space (FIG. 5A). However, subsequent stimulation with honeybee headspace was significantly inhibited in long-term (F(2,10)=14.3, p=0.001), similarly to the situation when both stimuli were applied together (F(2, 10)=25.6, p=0.0001). This inhibition was specific to the effect of compound, as none of this inhibition was observed in the control set of hexane given with honeybee headspace (F(2,10)=0.016, p=0.98). This activity differs from the effect of long-term inhibitors studied with gypsy moth antennae, in that those compounds were only inhibitory after a mixed stimulus and not by themselves. The longevity of the inhibitory effect of cy{4,1} was examined by varying time interval between the two sets of stimuli: "compound" and "bees after compound: 30, 45 or 60 s. The results suggest that the effect of the compound lasts for more than 60 s (30 s F(2, 10)=14.3, p=0.001; 45 s F(2, 10)=19.4, p=0.0004; 60 s F(2, 10)=11.8, p=0.002) (FIG. 5B).

The Effect of EAG Inhibiting Compounds on *Varroa* Host Selection

The mites' choice for nurse or a forager bee was significantly dependent on the treatment. As can be seen in FIG. 6B, after 180 min, in the presence of a solvent hexane (control) most of the mites (84%) chose the nurse bee, whereas in the presence of disrupting compound cy{4,1} only a minority of mites chose the nurse bee over the forager. The extent to which foragers were chosen over nurses was dose dependent: at 10 μg, about 94% of *Varroa* were found on the forager bee, while at 0.1 μg and 0.01 μg doses 75% and 71% of *Varroa* chose the forger bee, respectively (OR=82.8, (95% CI 19.2-456.2); FIG. 6B). Compounds 3b{2,2} and cy{2,2} exhibit a similar activity (OR=35.1, (95% CI 10.8-136.9); OR=54, (95% CI 15.3-231.9); FIG. 6C and FIG. 8), whereas compound 3c{2,2} did not alter the natural preference of the mites for nurse bees over foragers in (OR=5.41, (95% CI 1.7-18.3); FIG. 6D).

Figure 9:
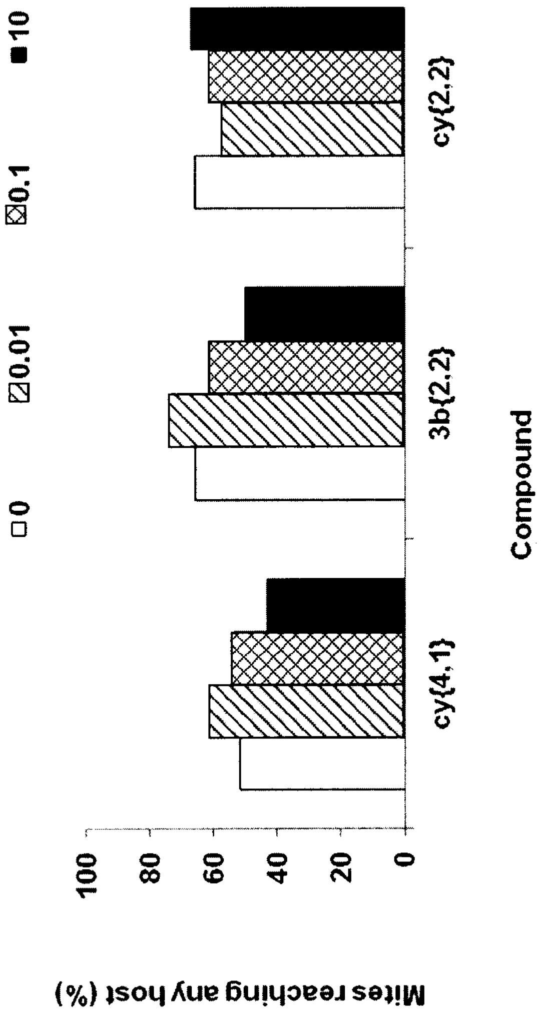
FIG. 9 shows the effect of embodiments of the compounds of the present disclosure on the percentage of mites reaching any of the hosts in the choice bioassay, 180 min from the beginning of the experiment. The data are percentage of viable mites in the presence of hexane (control) or disrupting compound at each of three tested doses (0.01 μg, 0.1 μg, 10 μg) Chi-square test, ns.

*Varroa* starts dispersing shortly after the beginning of the experiment, but even after 180 minutes only 43-73% of mites reached any of the hosts (FIG. 9). Only a few died during the experiment. However, there was no significant reduction in the ability of mites to reach any of the hosts in any of the treatments (Chi-square test, cy{4,1} $\chi^2$ (3)=2.01, n=192, p=0.57; 3b{2,2} $\chi^2$ (3)=3.9, n=180, p=0.27; cy{2,2} $\chi^2$ (3)=1.04, n=180, p=0.79).

Structure-Activity Relationship

FIG. 9 shows the effect of 3 selected compounds on the percentage of mites reaching any of the hosts in the choice bioassay, 180 min from the beginning of the experiment. The data are percentage of viable mites in the presence of hexane (control) or disrupting compound at each of three tested doses (0.01 μg, 0.1 μg, 10 μg) Chi-square test, ns. Molecular modelling overlay of energy minimized conformers of cy{4, 1} and 3b{2,2} was also conducted. Compounds cy{4,1} and 3b{2,2} were the most active congeners for both, long-term inhibition and mite host selection alteration. Assuming that they exert their effects at or near their energy minima, a distorted "V-shaped" active space was delineated by the overlaid structures of cy{4,1} and 3b{2,2}. The epitopes that seem to confer activity are: 1) a planar or nearly planar ring with π electron density, 2) the oxygen atoms of the ether moieties and 3) the alkyl substituents. The two most active compounds can place the ring and both oxygens in similar regions, relative to each other.

Inactive compounds either do not fill the active site (e.g., cy{1,1}) or cannot place both oxygens and the ring in the regions required for activity. E.g., 3c{1,3}(not shown), 3c{2,2}, 3c{2,3} were all inactive in both, long-term inhibition and mite host selection alteration. There appears to be some flexibility as to the extent to which both ether alkyl substituent pockets are filled. For example, cy{2,1} and cy{3,1} were both active as long-term inhibitors. However, there is a clear limit as to the size of the group the alkyl pockets can accommodate: cy{5,1} was too large and, therefore, not active. Compound 3a{2,2} has the two ethoxy groups too near to each other and, therefore, would place the second ethoxy group between the two pockets of the active space. This compound was not very active in long-term inhibition. Compound cy{2,2} presented an interesting case: it could fit into the active space with the stereochemistry at both chiral centers reversed. Even then, the ethyl group at position 1 of the cyclopentene ring projects outside of the alkyl pocket and, more importantly, the oxygen atoms are located at different positions from those in the overlaid cy{4,1} and 3b{2,2} space. Thus, compound cy{2,2} is moderately active, and the enantiomer that is active should be opposite to the active cy{4,1} enantiomer.

DEET (3-methyl-N,N-diethylbenzamide, a well-known insect repellent) has been tested in a separate study, and was found to long-term inhibit the *Varroa*'s response to bee headspace at a high dose, while short-term inhibition was not significant. Interestingly, DEET did not fit into the active space delineated by the two most active long-term inhibitors and host-preference-altering compounds, cy{4,1} and 3b{2, 2}, as evaluated by molecular modelling.

Taken together, these data suggest that long-term inhibition in the electrophysiological assay is a good predictor for alteration of host selection in the behavioural assay and that the active space delineated by long-term inhibition is also the active space for the alteration of the mite's host selection preference.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of treating *Varroa destructor* infection of a bee colony, comprising:

(A) providing a compound of Formula (II):

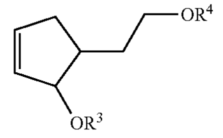

(II)

wherein:

$R^3$ is selected from $C_{1-6}$ alkyl and $C_{2-6}$ alkenyl, and $R^4$ is selected from $C_{1-6}$ alkyl and $C_{2-6}$ alkenyl; and (B) placing the compound of Formula (II) in a bee colony enclosure.

2. The method of claim 1, wherein $R^3$ is $C_{1-3}$ alkyl.

3. The method of claim 1, wherein $R^4$ is methyl or ethyl.

4. The method of claim 1, wherein $R^4$ is methyl.

5. The method of claim 1, further comprising applying (A) a compound of Formula (I):

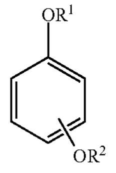

(I)

wherein:

$OR^2$ is an ortho, meta, or para substituent relative to OR', $R^1$ is selected from $C_{1-6}$ alkyl and $C_{2-6}$ alkenyl, and $R^2$ is selected from $C_{1-6}$ alkyl and $C_{2-6}$ alkenyl;

(B) a compound of Formula (Ic):

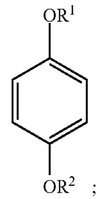

(Ic)

;

or (C) a compound of Formula (II):

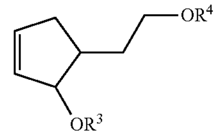

(II)

wherein:

$R^3$ is selected from $C_{1-6}$ alkyl and $C_{2-6}$ alkenyl, and $R^4$ is selected from $C_{1-6}$ alkyl and $C_{2-6}$ alkenyl;

to a brood cell in a bee colony enclosure.

6. The method according to claim 1, further comprising removing a drone brood comb from the bee colony enclosure after placing the compound of Formula (II) in a bee colony enclosure, or further comprising heat-treating a drone trapping comb after placing the compound of Formula (II) in a bee colony enclosure, or further comprising removing and heat-treating worker bees after placing the compound of Formula (II) in a bee colony enclosure, or further comprising confining a queen bee prior to, during, or after placing the compound of Formula (II) in a bee colony enclosure, or further comprising placing a sticky mite-trapping bottom board in a bee colony enclosure, or any combination thereof.

* * * * *

UNITED STATES PATENT AND TRADEMARK OFFICE

CERTIFICATE OF CORRECTION

PATENT NO. : 10,022,338 B2
APPLICATION NO. : 15/128870
DATED : July 17, 2018
INVENTOR(S) : E. Plettner et al.

It is certified that error appears in the above-identified patent and that said Letters Patent is hereby corrected as shown below:

On the Title Page

| | | |
|---|---|---|
| Item (71) Column 1 | Applicants 2nd applicant | "**AGRICULTURAL & RURAL DEVELOPMENT**" should read --**AGRICULTURE & RURAL DEVELOPMENT**-- |

In the Claims

| | | |
|---|---|---|
| Column 30 (Claim 5, Line 5) | Line 33 | "relative to OR'," should read --relative to $OR^1$,-- |

Signed and Sealed this
Twenty-sixth Day of March, 2019

Andrei Iancu
*Director of the United States Patent and Trademark Office*